(12) United States Patent
Racz et al.

(10) Patent No.: US 11,318,299 B2
(45) Date of Patent: May 3, 2022

(54) VISUAL IMPLANT

(71) Applicant: THE FRANCIS CRICK INSTITUTE LIMITED, London (GB)

(72) Inventors: Romeo-Robert Racz, London (GB); Gabriella Racz, London (GB); Andreas Schaefer, London (GB)

(73) Assignee: The Francis Crick Institute Limited, London (GB)

( * ) Notice: Subject to any disclaimer, the term of this patent is extended or adjusted under 35 U.S.C. 154(b) by 112 days.

(21) Appl. No.: 16/964,343

(22) PCT Filed: Jan. 23, 2019

(86) PCT No.: PCT/GB2019/050180
§ 371 (c)(1),
(2) Date: Jul. 23, 2020

(87) PCT Pub. No.: WO2019/145705
PCT Pub. Date: Aug. 1, 2019

(65) Prior Publication Data
US 2021/0046304 A1 Feb. 18, 2021

(30) Foreign Application Priority Data
Jan. 26, 2018 (GB) .................................... 1801320

(51) Int. Cl.
*A61N 1/05* (2006.01)
*A61N 1/36* (2006.01)
*A61N 1/372* (2006.01)

(52) U.S. Cl.
CPC ....... *A61N 1/0543* (2013.01); *A61N 1/36046* (2013.01); *A61N 1/36157* (2013.01); *A61N 1/37223* (2013.01)

(58) Field of Classification Search
CPC .............. A61N 1/0543; A61N 1/36046; A61N 1/36157; A61N 1/37223; H01L 2224/45565
See application file for complete search history.

(56) References Cited

U.S. PATENT DOCUMENTS

| 6,647,297 B2 | 11/2003 | Scribner |
| 2002/0111655 A1 | 8/2002 | Scribner |
| 2007/0005116 A1 | 1/2007 | Lo |

(Continued)

FOREIGN PATENT DOCUMENTS

WO 2012/058477 5/2012

OTHER PUBLICATIONS

Combined Search and Examination Report for GB Application No. 1801320.1 dated Jun. 28, 2018, 7 pages.

(Continued)

*Primary Examiner* — Eugene T Wu
(74) *Attorney, Agent, or Firm* — Nixon & Vanderhye P.C.

(57) ABSTRACT

A visual implant (2) comprises an array of micro-electrodes (4) including at least two stimulation micro-electrodes each comprising: a core (106) of conducting material; insulating material (108) surrounding the core; and a layer (112) of metal or metal oxide nano-structures deposited on tips of the micro-electrodes at a front end for interfacing with a target site for visual stimulation; and an integrated circuit (6) to control a pattern of stimulation current driven through the array of micro-electrodes.

20 Claims, 24 Drawing Sheets

(56) References Cited

U.S. PATENT DOCUMENTS

| | | | |
|---|---|---|---|
| 2009/0011536 | A1 | 1/2009 | Zhang et al. |
| 2009/0248113 | A1 | 10/2009 | Nimer |
| 2011/0172736 | A1 | 7/2011 | Gefen et al. |
| 2011/0208031 | A1 | 8/2011 | Wolfe |
| 2011/0233075 | A1 | 9/2011 | Soleymani |
| 2012/0259410 | A1 | 10/2012 | Gefen et al. |
| 2014/0371564 | A1 | 12/2014 | Anikeeva |
| 2015/0209586 | A1 | 7/2015 | Silva et al. |
| 2016/0128588 | A1 | 5/2016 | Melosh et al. |
| 2018/0067075 | A1* | 3/2018 | Racz ............... C25D 13/20 |

OTHER PUBLICATIONS

International Search Report and Written Opinion of the ISA for PCT/GB2019/050180 dated Apr. 10, 2019, 14 pages.

N.A. Alba et al, "In Vitro Electrochemical Analysis of a PEDOT/MWCNT Neural Electrode Coating" *Biosensors*, 2015, 5, Oct. 13, 2015, pp. 618-646.

C. Boehler et al, "Nanostructured platinum grass enables superior impedance reduction for neural microelectrodes" *Biomaterials*, 67, Jul. 21, 2015, pp. 346-353.

Ch. Broennimann et al., "Development of an Indium bump bond process for silicon pixel detectors at PSI" *Nuclear Instruments and Methods in Physics Research A*, May 26, 2006, pp. 303-308.

N.M. Carretero et al, "Enhanced Charge Capacity in Iridium Oxide-Graphene Oxide Hybrids" *Electrochimica Acta*, accepted Oct. 10, 2014, pp. 1-17.

I.G. Casella et al., "Anodic electrodeposition of iridium oxide particles on glassy carbon surfaces and their electrochemical/SEM/XPS characterization" *Journal of Electroanalytical Chemistry*, 736, Nov. 15, 2014, pp. 147-152.

E. Castagnola et al, "pHEMA Encapsulated PEDOT-PSS-CNT Microsphere Microelectrodes for Recording Single Unit Activity in the Brain" *Frontiers in Neuroscience*, 10, Apr. 18, 2016, pp. 1-14.

H. Charkhkar et al, "Chronic intracortical neural recordings using microelectrode arrays coated with PEDOT-TFB" *Acta Biomaterialia*, 32, Dec. 12, 2015, pp. 57-67.

T. Chung et al, "Electrode modifications to lower electrode impedance and improve neural signal recording sensitivity" *Journal of Neural Engineering*, 12 (2015), Sep. 23, 2015, pp. 1-14.

S.F. Cogan, "Neural Stimulation and Recording Electrodes" *Biomedical Engineering*, 10, Apr. 22, 2008, pp. 275-309.

J.E. Ferguson et al, "Creating low-impedance tetrodes by electroplating with additives" *Sensors and Actuators A: Physical*, 156, Oct. 9, 2009, pp. 388-393.

C.-C. Hu et al, "Cyclic voltammetric deposition of hydrous ruthenium oxide for electrochemical capacitors: effects of codepositing iridium oxide" *Electrochimica Acta*, 45 (2000) Jan. 24, 2000, pp. 2685-2696.

E.W. Keefer et al, "Carbon nanotube coating improves neuronal recordings" *Nature Nanotechnology*, vol. 3, Jul. 2008, pp. 434-439.

K. Kondo et al, "Copper Electrodeposition for Nanofabrication of Electronic Devices" Nanostructure Science and Technology, Nov. 20, 2013, pp. 1-282.

T.D.Y. Kozai et al, "Chronic in vivo evaluation of PEDOT/CNT for stable neural recordings" *IEEE Transactions on Biomedical Engineering*, 63(1), Jun. 15, 2015, pp. 1-9.

T.D.Y. Kozai et al, "Ultrasmall implantable composite microelectrodes with bioactive surfaces for chronic neural interfaces" *Nature Materials*, vol. 11, Nov. 11, 2012, pp. 1065-1073.

T.D.Y. Kozai et al, "Two-photon imaging of chronically implanted neural electrodes: Sealing methods and new insights" *Journal of Neuroscience Methods*, 258 (2016), available online Oct. 23, 2015, pp. 46-55.

D. Kuzum et al, "Transparent and flexible low noise graphene electrodes for simultaneous electrophysiology and neuroimaging" *Nature Communications*, 5, Oct. 20, 2014, pp. 1-10.

G. Lee et al, "Fabrication, structure and mechanical properties of indium nanopillars" *Acta Materialia* 58 (2010) available online Nov. 20, 2009, pp. 1361-1368.

Y. Lu et al, "Anodically electrodeposited iridium oxide films microelectrodes for neural microstimulation and recording" *Sensors and Actuators B: Chemical*, 137, Dec. 9, 2008, pp. 334-339.

S.C. Mailley et al, "Electrochemical and structural characterizations of electrodeposited iridium oxide thin-film electrodes applied to neurostimulating electrical signal" *Materials Science and Engineering*, 21 (2002), Sep. 2002, pp. 167-175.

R.D. Meyer et al, "Electrodeposited Iridium Oxide for Neural Stimulation and Recording Electrodes" *IEEE Transactions on Neural Systems and Rehabilitation Engineering*, vol. 9, No. 1, Mar. 2001, pp. 2-11.

D.-W. Park et al, "Graphene-based carbon-layered electrode array technology for neural imaging and optogenetic applications" *Nature Communications* 5, Oct. 20, 2014, pp. 1-11.

M.R. Pinnel et al, "Oxidation of Copper in Controlled Clean Air and Standard Laboratory Air at 50° C. to 150° C." *Applications of Surface Science* vol. 2, Issue 4 (1979), May 1979, pp. 558-577.

R.P. Reed et al, "Tensile Strength and Ductility of Indium" *Materials Science and Engineering A*, 102, Feb. 11, 1988, pp. 227-236.

P. Steegstra et al, "Influence of oxidation state on the pH dependence of hydrous iridium oxide films" *Electrochimica Acta*, 76, May 15, 2012, pp. 26-33.

Yingtao Tian et al, "Electrodeposition of Indium for Bump Bonding" *Proceedings 2008 Electronic Components and Technology Conference* (ECTC 2008), Jun. 2008, pp. 2096-2100.

S. Venkatraman et al, "In Vitro and In Vivo Evaluation of PEDOT Microelectrodes for Neural Stimulation and Recording" *IEEE Transactions on Neural Systems and Rehabilitation Engineering*, vol. 19, No. 3, Jun. 2011, pp. 307-316.

M.T. Wang et al, "Barrier Properties of Very Thin Ta and TaN Layers Against Copper Diffusion" *Journal of The Electrochemical Society*, vol. 145, No. 7, Jul. 1998, pp. 2538-2545.

S.J. Wilks et al, "Poly(3,4-ethylenedioxythiophene) as micro-neural interface material for electrostimulation" *Frontiers in Neuroengineering*, vol. 2, Article 7, Jun. 9, 2009, pp. 1-8.

D.O. Wipf et al, "Microdisk electrodes: Part II. Fast-scan cyclic voltammetry with very small electrodes" *Journal of Electroanal. Chem.*, Mar. 30, 1989, pp. 15-25.

K. Yamanaka, "Anodically Electrodeposited Iridium Oxide Films (AEIROF) from Alkaline Solutions for Electrochromic Display Devices" *Japanese Journal of Applied Physics*, vol. 28, No. 4, Apr. 1989, pp. 632-637.

E. Castagnola et al, "Smaller, softer, lower-impedance electrodes for human neuroprosthesis: a pragmatic approach" Frontiers in Neuroengineering, vol. 7, article 8, pp. 1-17, Apr. 2014.

Canales Andres et al., "Multifunctional fibers for simultaneous optical, electrical and chemical interrogation of neural circuits in vivo", Nature Biotechnology, vol. 33, No. 3, pp. 277-284 (Mar. 2015).

Liao Yi-Fang et al., "A simple method for fabricating microwire tetrode with sufficient rigidity and integrity without a heat-fusing process", Journal of Neuroscience Methods, vol. 195, pp. 211-215 (2011).

S.K. Arya et al., "Effects of the Electrode Size and Modification Protocol on a Label-Free Electrochemical Biosensor" *Langmuir* 2013, vol. 29, May 7, 2013, pp. 6770-6777.

J. Delbeke et al, "Position, size and luminosity of phosphenes generated by direct optic nerve stimulation" *Vision Research*, vol. 43, Apr. 2003, pp. 1091-1102.

X. Fang et al, "Direct stimulation of optic nerve by electrodes implanted in optic disc of rabbit eyes" *Graefe's Arch Clin Exp Ophthalmol*, 243, Sep. 2004, pp. 49-56.

X. Fang et al, "Electrophysiological and histological studies of chronically implanted intrapapillary microelectrodes in rabbit eyes" *Graefe's Arch Clin Exp Ophthalmol*, 244, Aug. 2005, pp. 364-375.

A. Kaushik et al, "Nano-biosensors to detect beta-amyloid for Alzheimer's disease management" *Biosens Bioelectron*, 80, Jun. 15, 2016, pp. 1-39.

M. Kollo et al, "Scalable bundle design for large scale neuronal recordings in vivo" Berstein Conference, Sep. 2015, 1 page.

(56) References Cited

OTHER PUBLICATIONS

M. Koronyo-Hamaoui et al., "Identification of Amyloid Plaques in Retinas from Alzheimer's Patients and Noninvasive In Vivo Optical Imaging of Retinal Plaques in a Mouse Model" *Neuroimage*, Jan. 2011, pp. 1-27.

A. J. Muller et al, "First Clinical Evaluation of a New Long-Term Subconjunctival Glucose Sensor" *Journal of Diabetes Science and Technology*, vol. 6, Issue 4, Jul. 2012, pp. 875-883.

K. Nishida et al, "Biocompatibility and durability of Teflon-coated platinum-iridium wires implanted in the vitreous cavity" *J. Artif Organs*, vol. 14, Jul. 19, 2011, pp. 357-363.

K. Nishida et al, "Visual Sensation by Electrical Stimulation Using a New Direct Optic Nerve Electrode Device" *Brain Stimulations*, vol. 8, Letters to the Editor, Mar. 2015, 4 pages.

N.S. Oliver et al, "Glucose sensors: a review of current and emerging technology" *Diabetic Medicine*, vol. 26, Feb. 28, 2009, pp. 197-210.

H. Sakaguchi et al, "Electrical Stimulation with a Needle-type Electrode Inserted into the Optic Nerve in Rabbit Eyes" *Jpn J Ophthalmol*, Nov. 2004, vol. 48, pp. 552-557.

H. Sakaguchi et al., "Artificial vision by direct optic nerve electrode (AV-DONE) implantation in a blind patient with retinitis pigmentosa" *J Artif Organs*, vol. 12, Sep. 2009, pp. 206-209.

H. Sakaguchi et al, "Implantation of a newly developed direct optic nerve electrode device for artificial vision in rabbits" *J Artif Organs*, vol. 15, Apr. 2012, pp. 295-300.

T. Shalaby et al, "Targeting cerebrospinal fluid for discovery of brain cancer biomarkers" *Journal of Cncer Metastasis and Treatment*, vol. 2, May 18, 2016, pp. 176-187.

\* cited by examiner

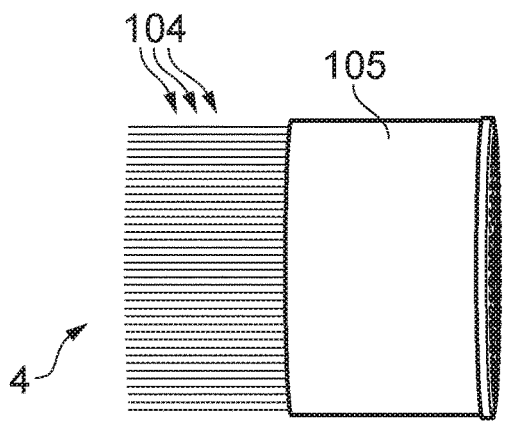
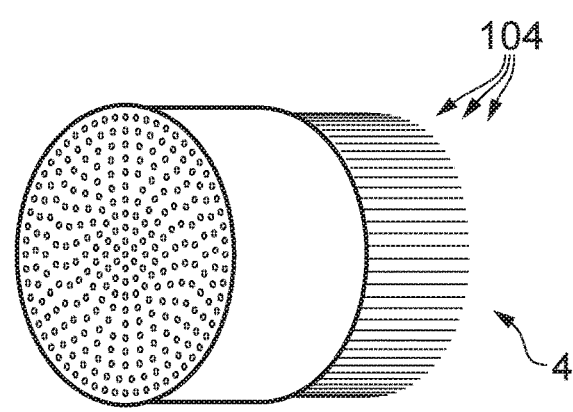
FIG. 2  FIG. 3
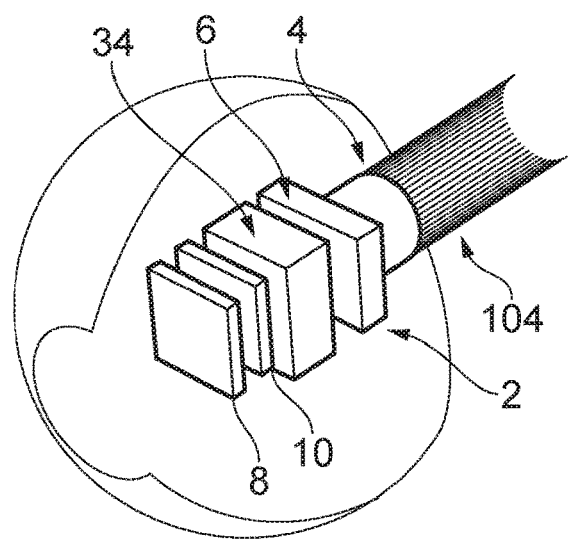
FIG. 4
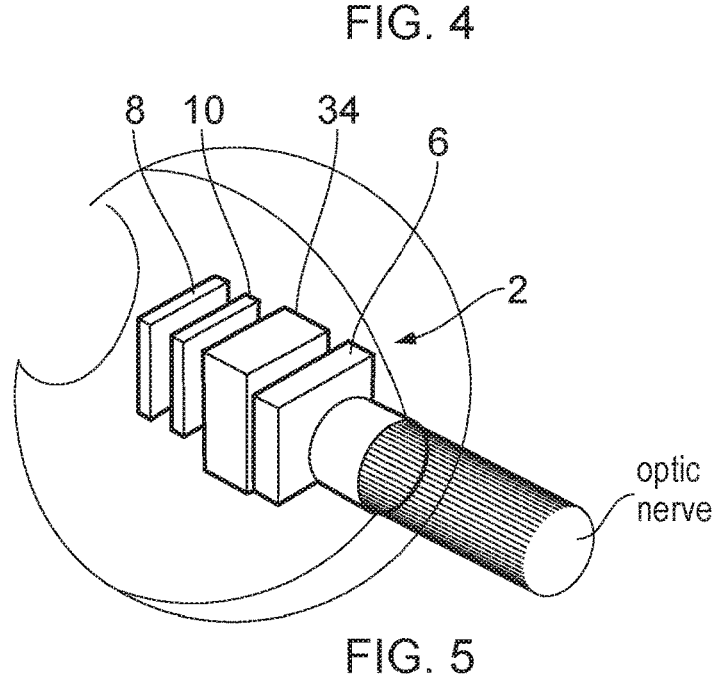
FIG. 5

VISUAL IMPLANT

This application is the U.S. national phase of International Application No. PCT/GB2019/050180 filed Jan. 23, 2019 which designated the U.S. and claims priority to GB Patent Application No. 1801320.1 filed Jan. 26, 2018, the entire contents of each of which are hereby incorporated by reference.

The present technique relates to the field of visual implants.

Blindness is a sensory loss with major negative impact on the individual's quality of life. An estimated 39 million people are affected worldwide, with numbers likely to increase given the demographic ageing and the increasing incidence of diabetes-related conditions. Potential treatment options include direct electrical stimulation of healthy parts of the visual pathway. Retinal stimulation can elicit useful visual sensation in patients with retinitis pigmentosa, however loss of ganglion cells precludes this approach. The optic nerve, lateral *geniculate* nucleus and visual cortex represent feasible stimulation targets.

At least some examples provide a visual implant comprising:
an array of micro-electrodes including at least two stimulation micro-electrodes each comprising:
a core of conducting material;
insulating material surrounding the core; and
a layer of metal or metal oxide nano-structures deposited on tips of the micro-electrodes at a front end for interfacing with a target site for visual stimulation; and
an integrated circuit to control a pattern of stimulation current driven through the array of micro-electrodes.

Further aspects, features and advantages of the present technique will be apparent from the following description of examples, which is to be read in conjunction with the accompanying drawings, in which:

FIGS. 2 and 3 show two views of a micro-electrode array used in the implant;

FIGS. 4 and 5 show examples of the implant when implanted into the fundus of an eye;

Figure 1:
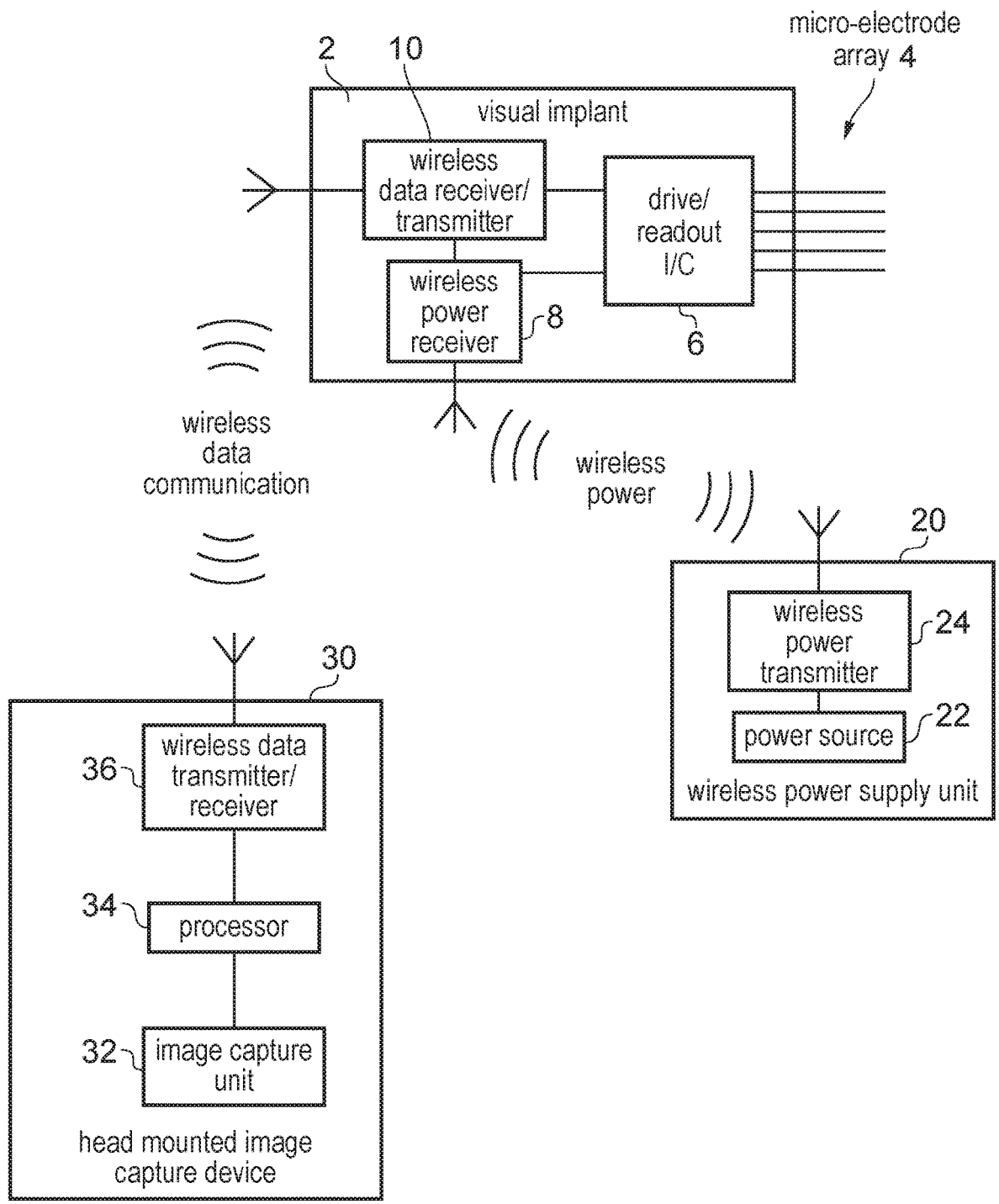
FIG. 1 illustrates a first example of a system comprising a visual implant, in which the visual implant receives image information transmitted wirelessly from a head mounted image capture device.
Figure 10:
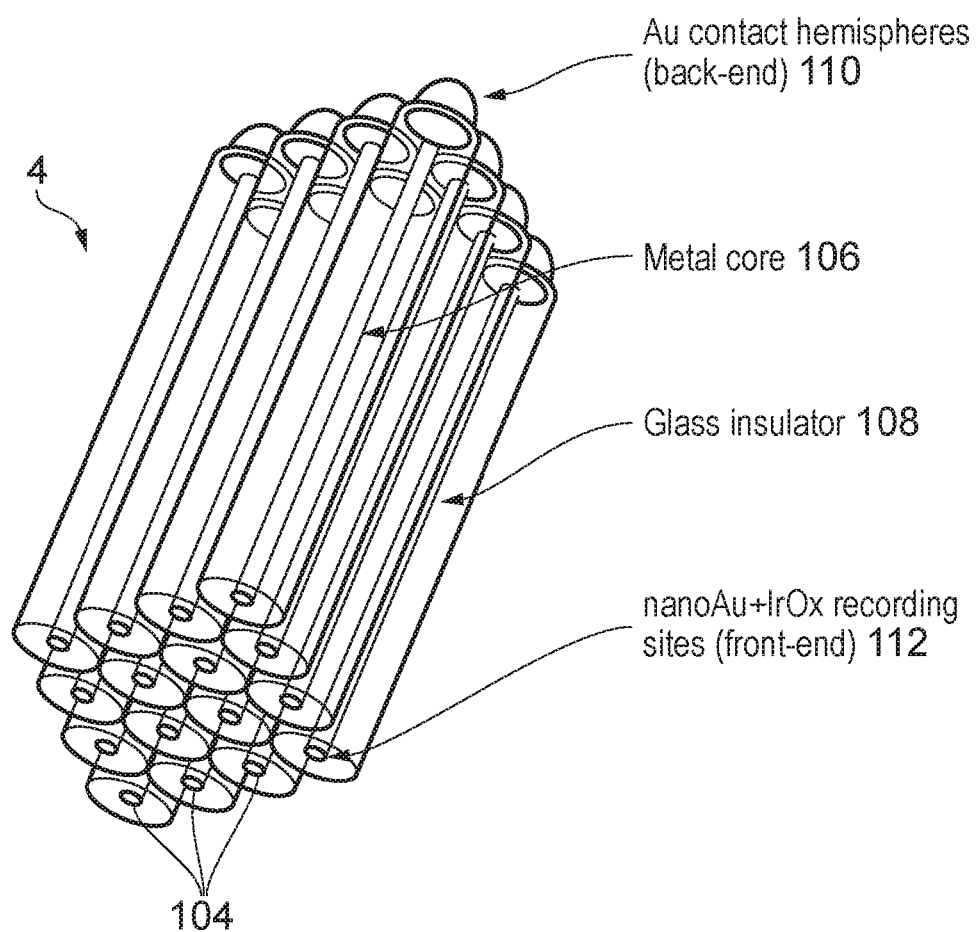
Figure 11:
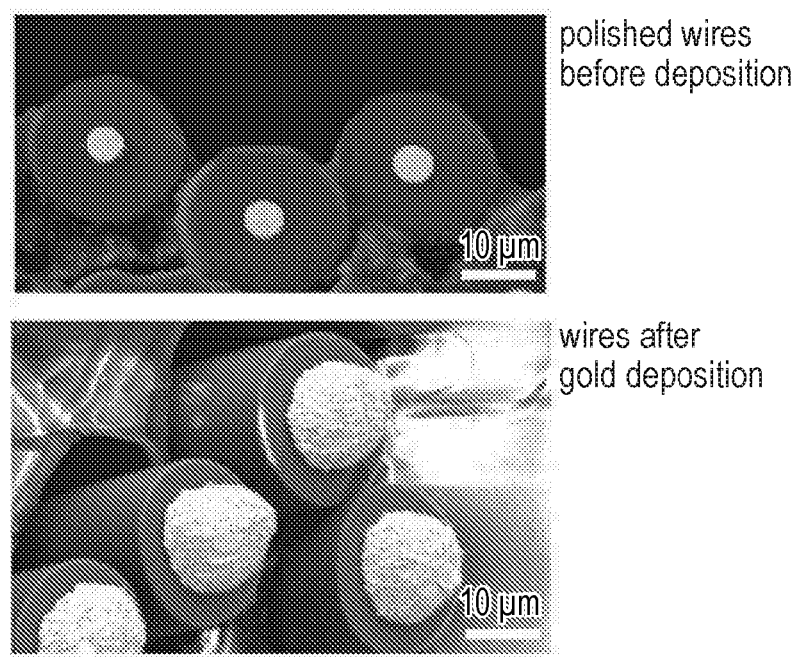
Figure 12:
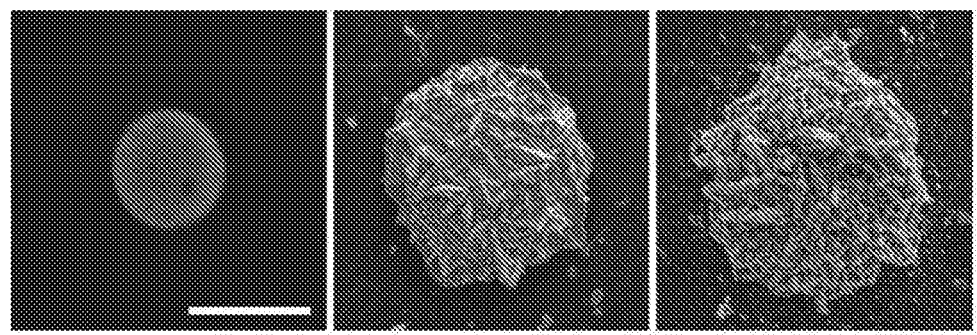
Figure 13:
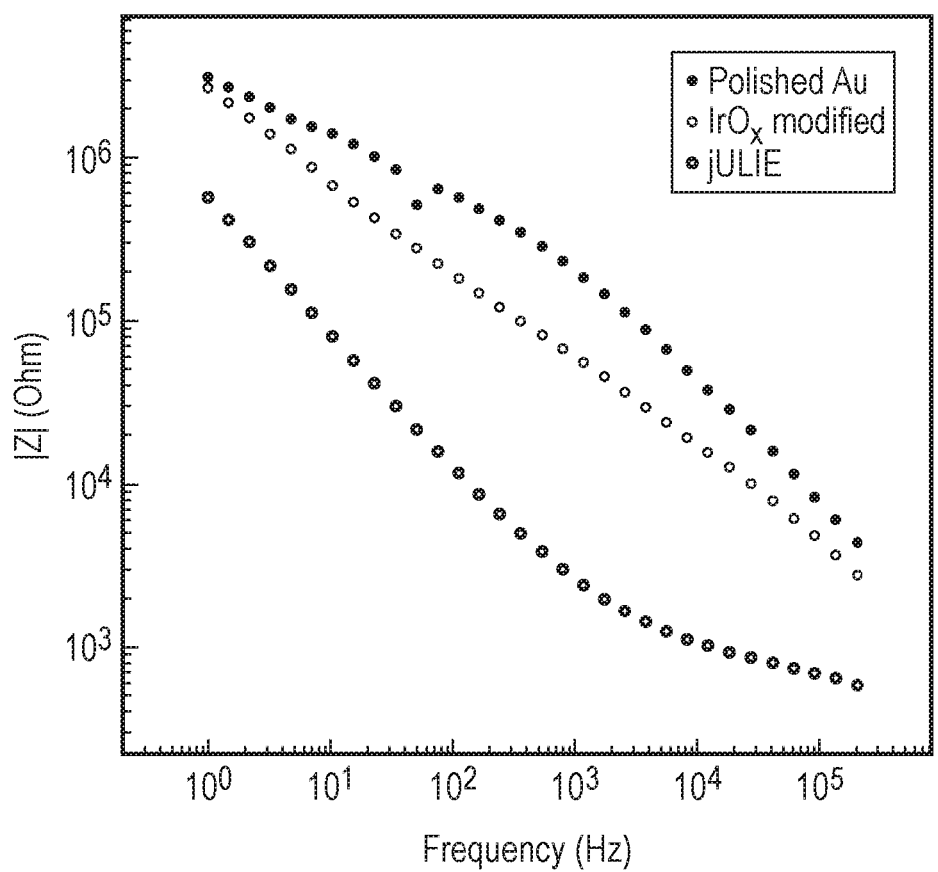
Figure 14:
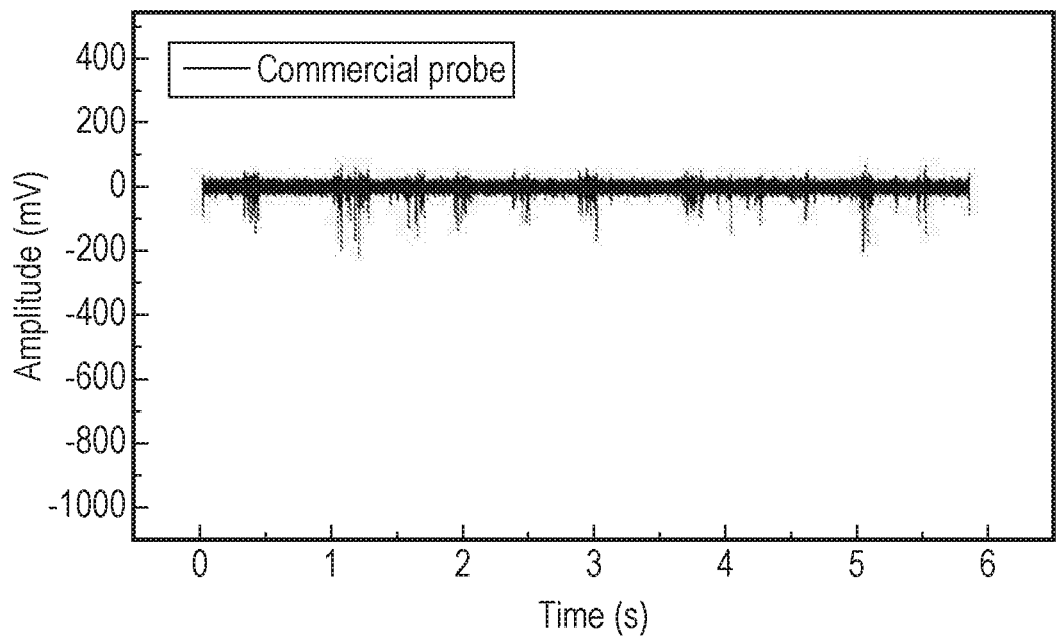
Figure 15:
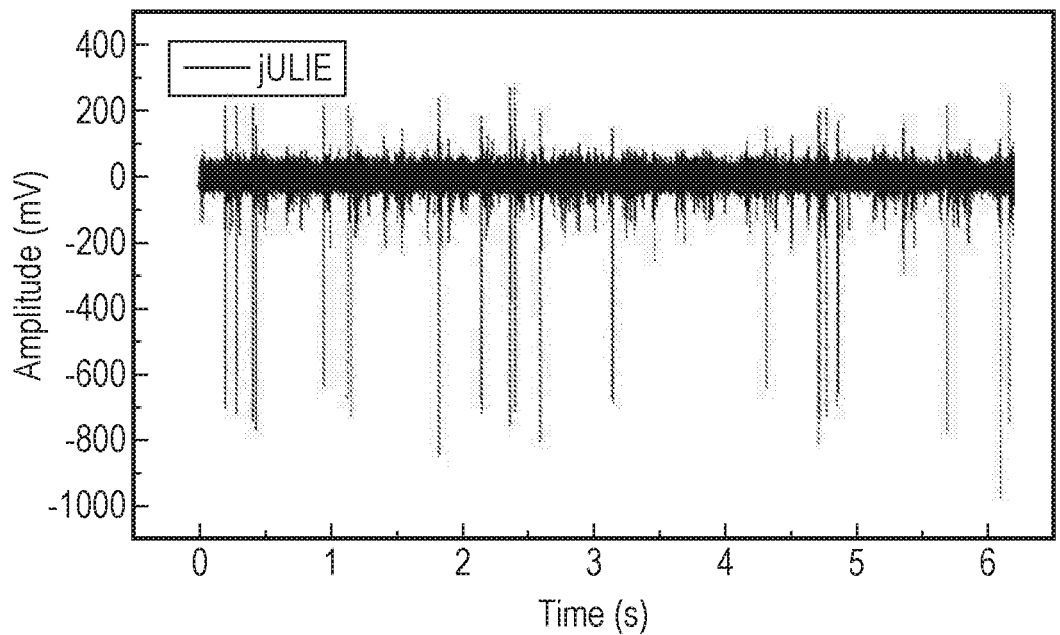
Figure 16:
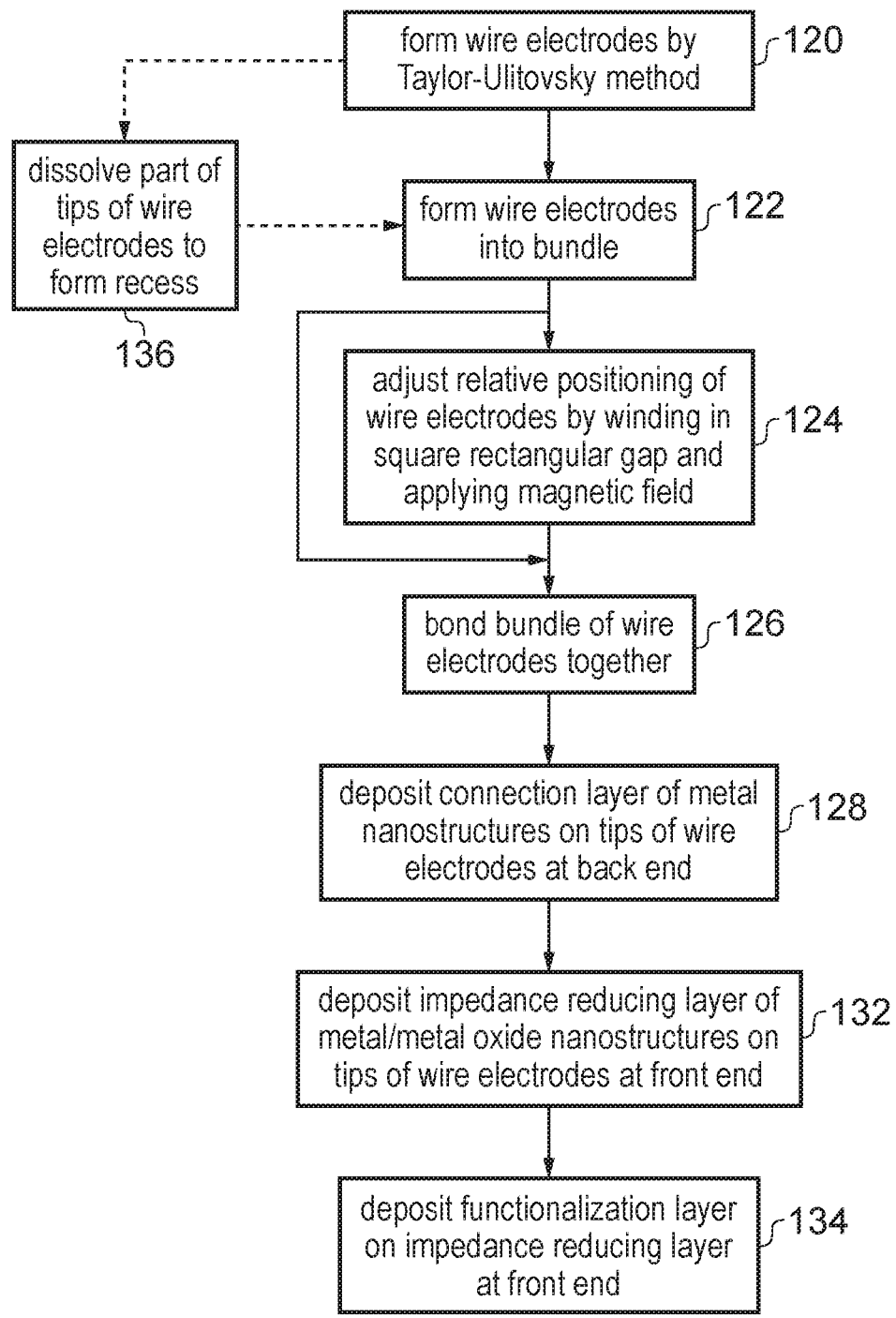
Figure 17:
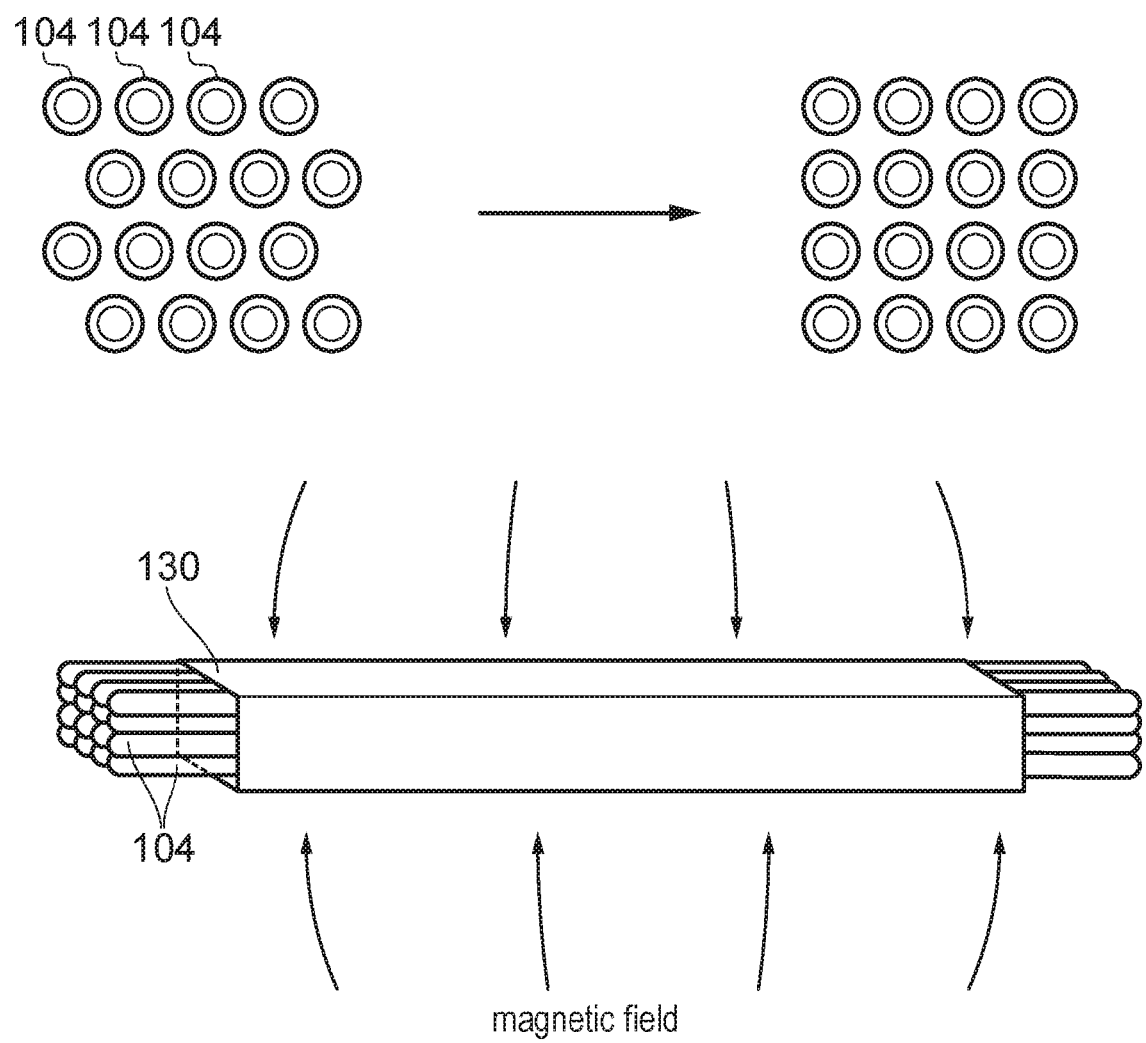
Figure 18:
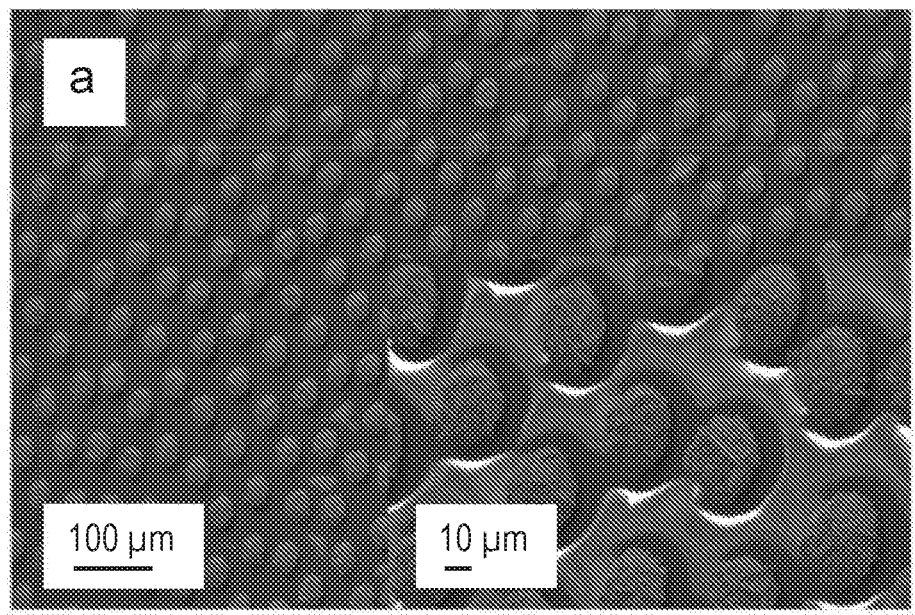
Figure 19:
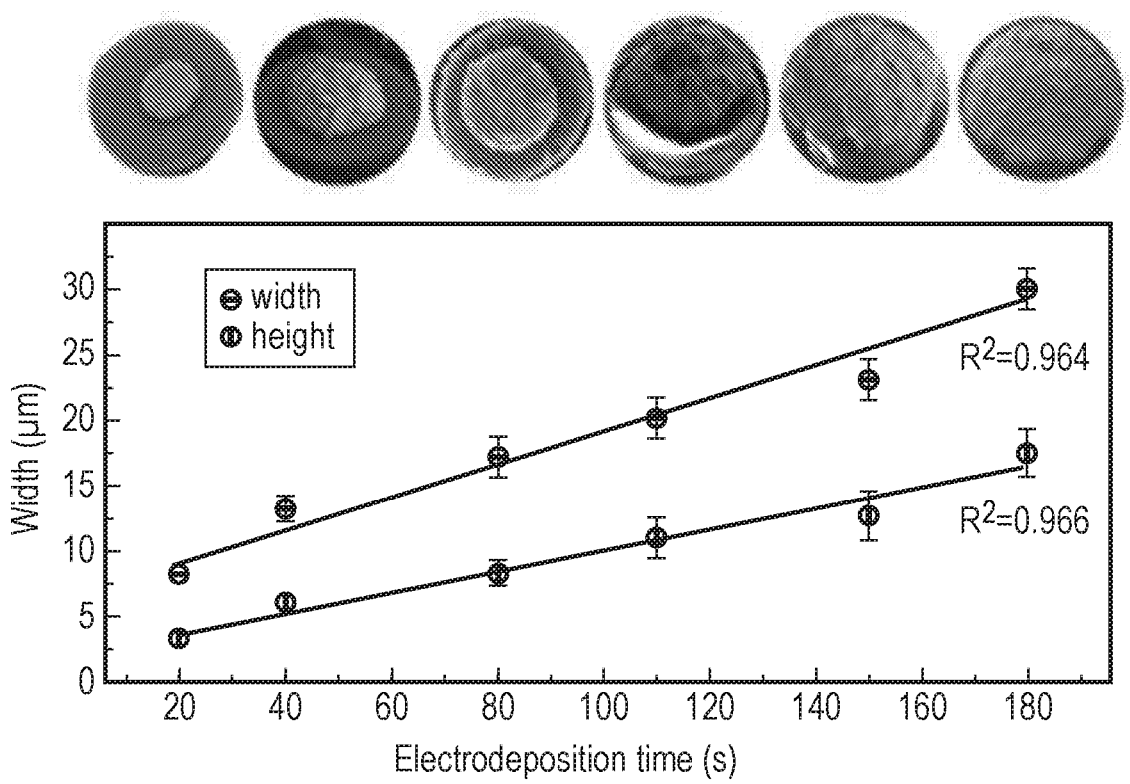
Figure 20:
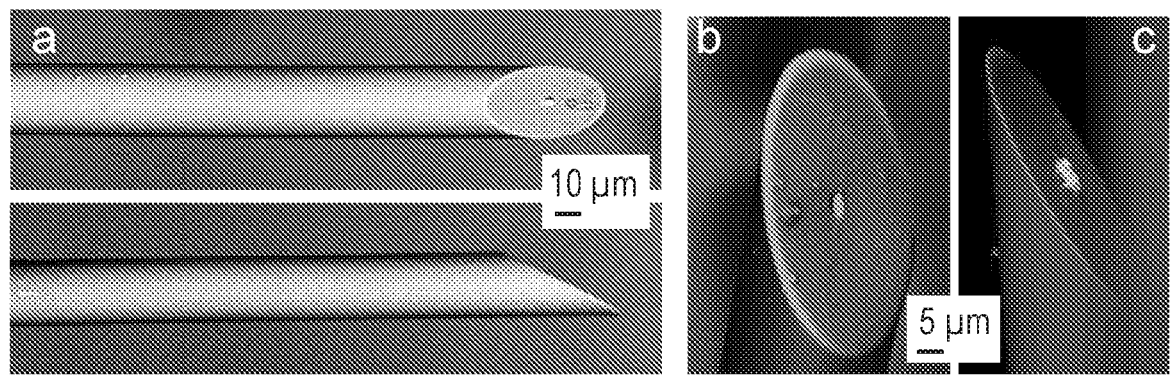
Figure 21:
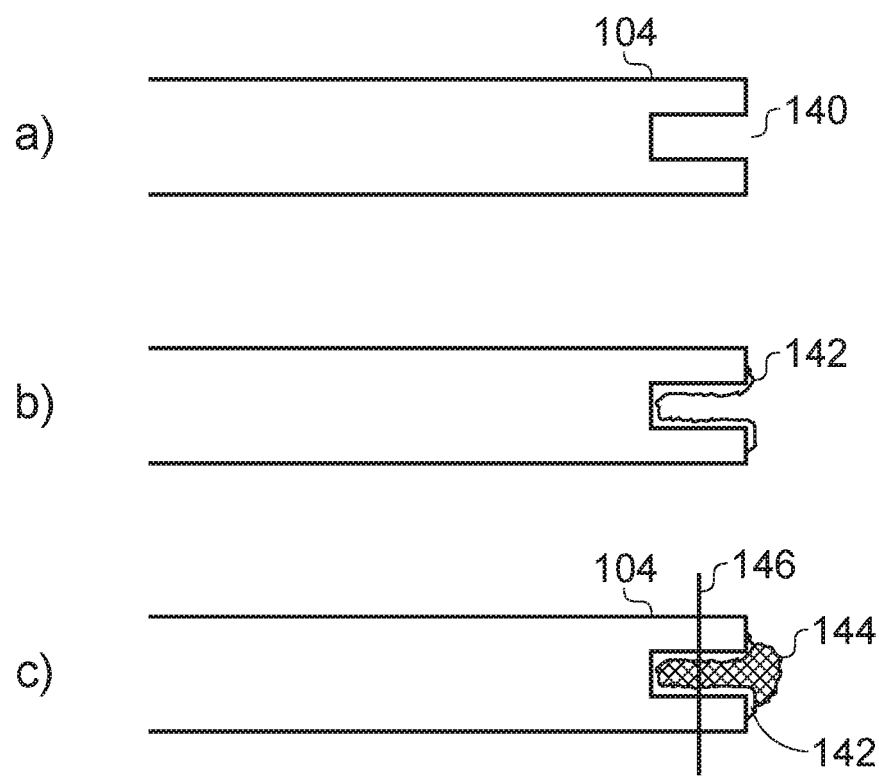
Figure 22:
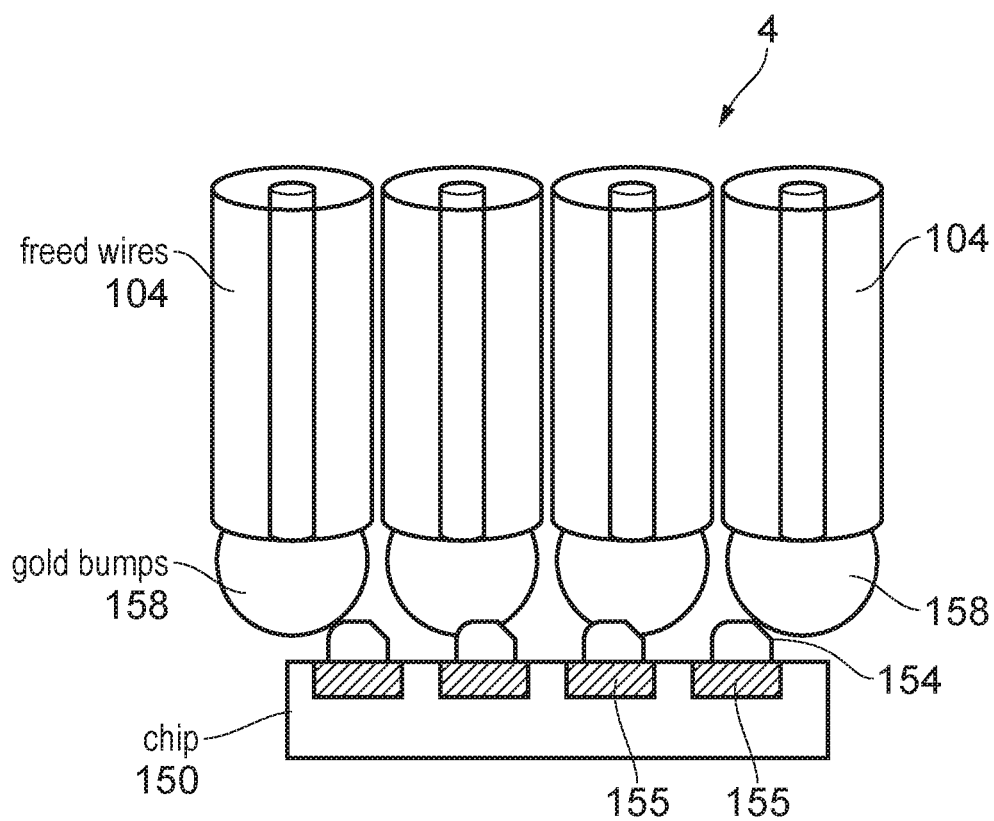
Figure 23:
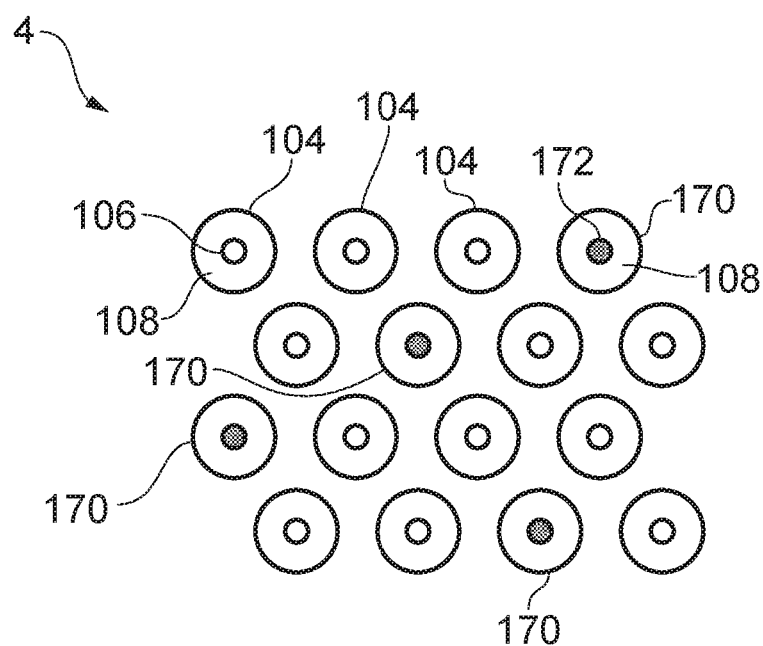
Figure 24:
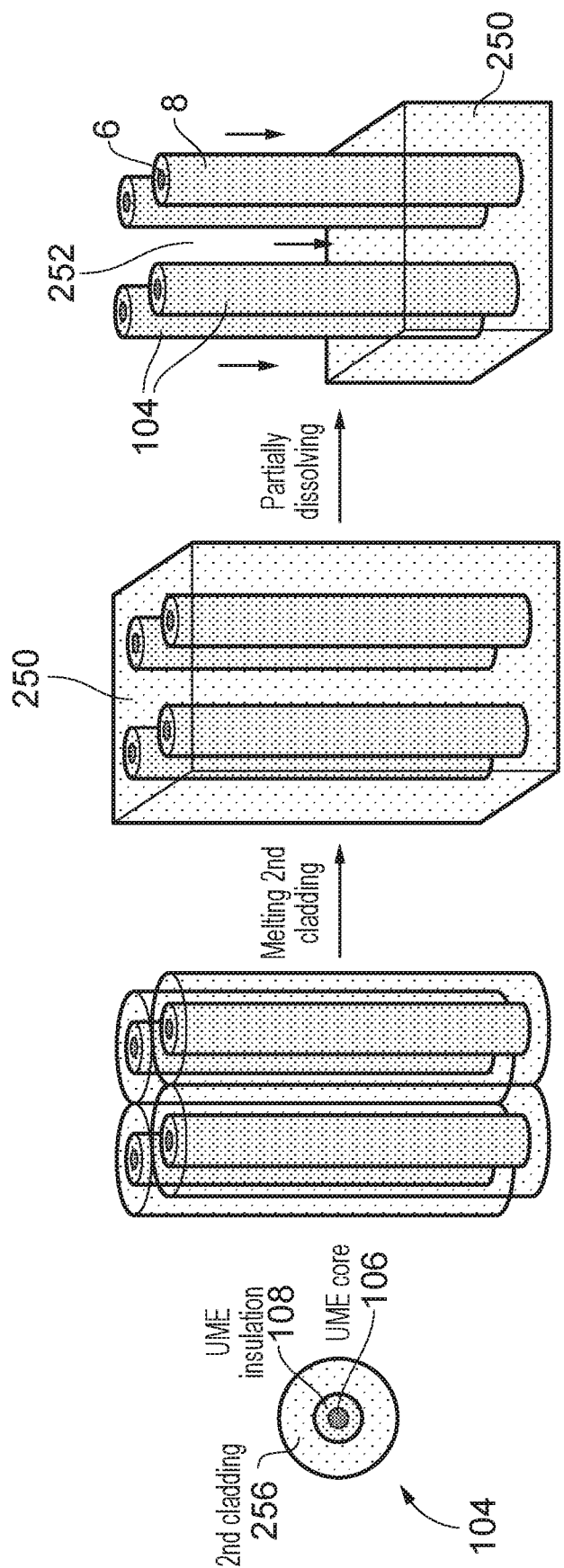
Figure 25:
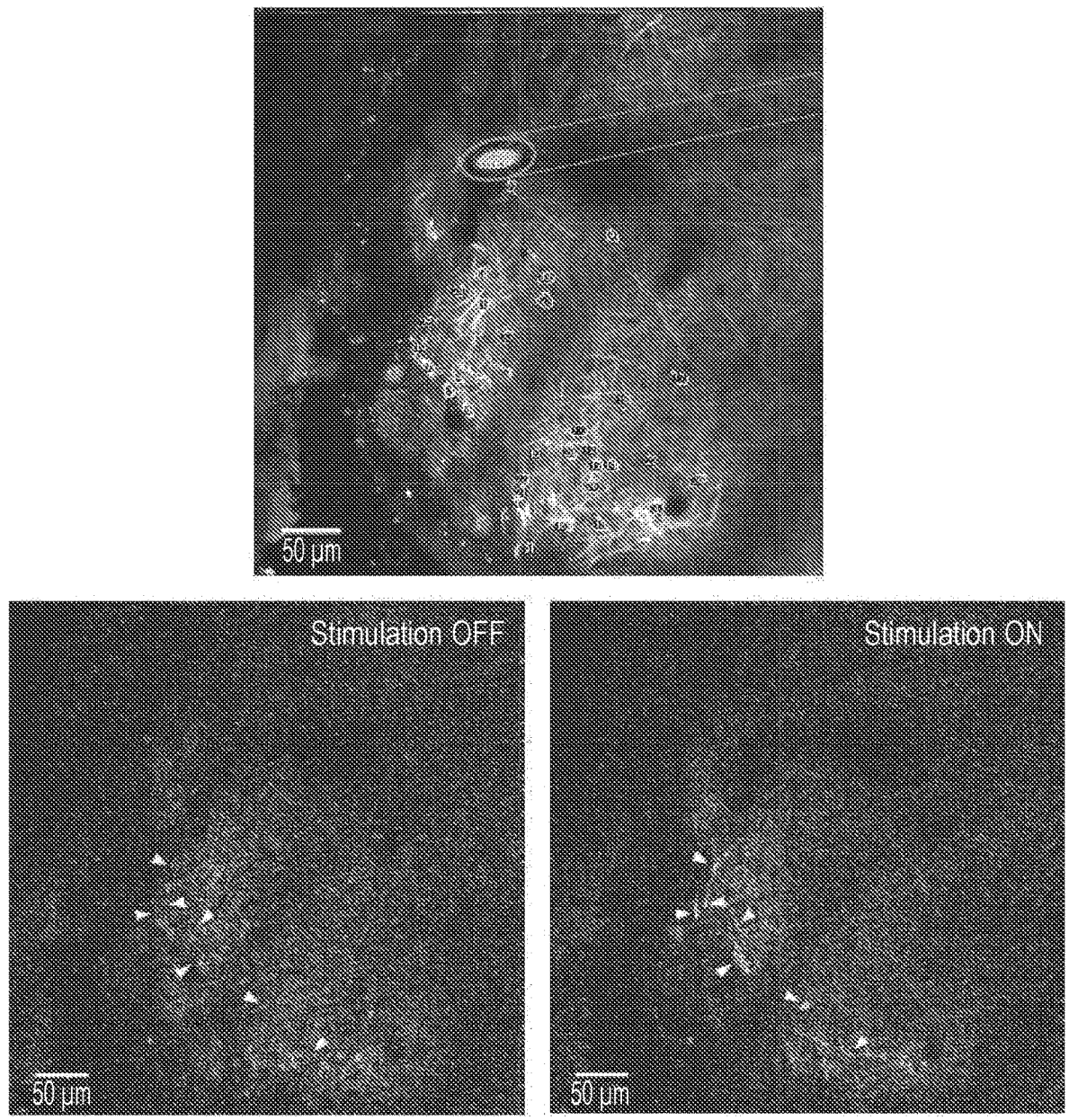
Figure 26:
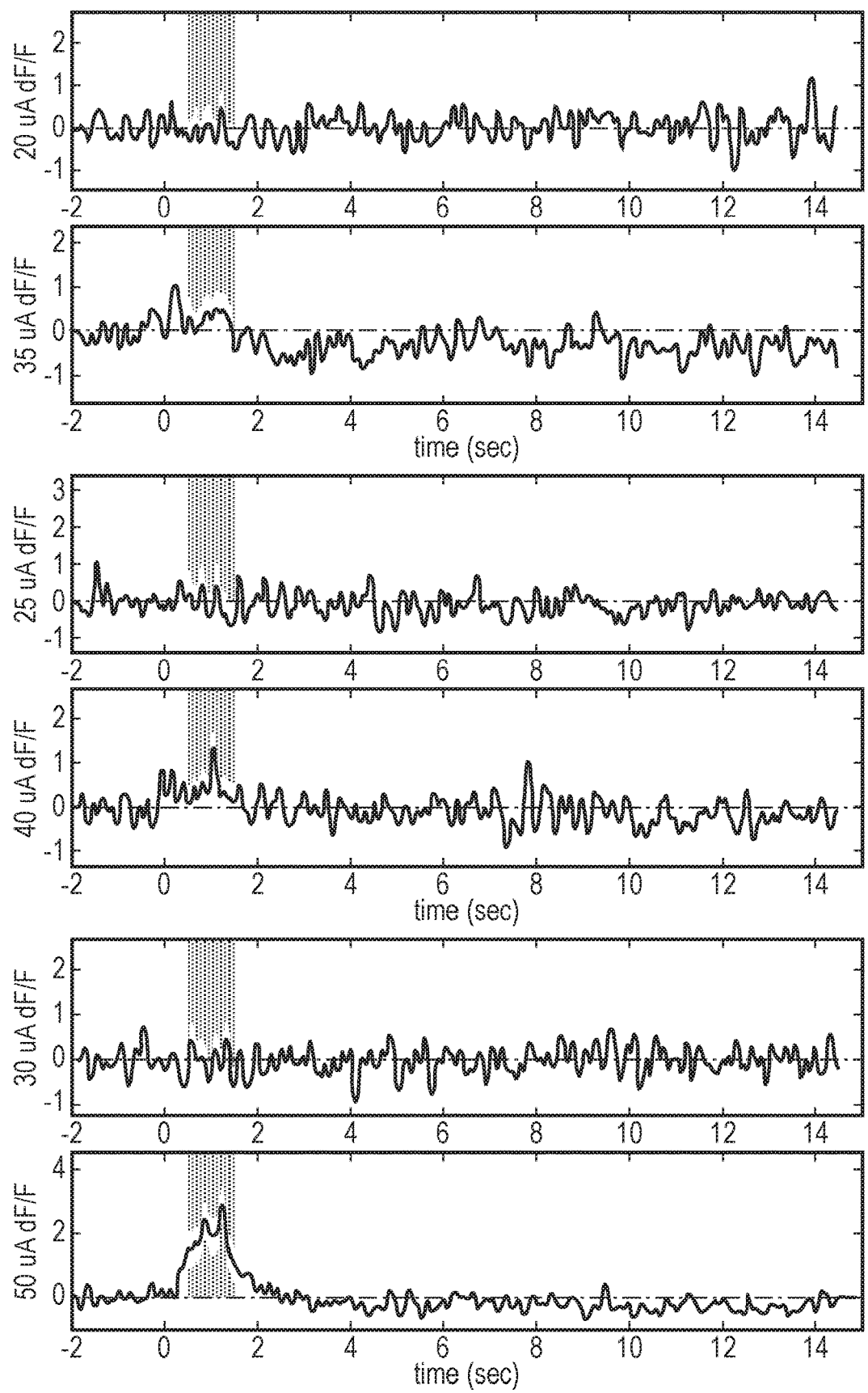
Figure 27:
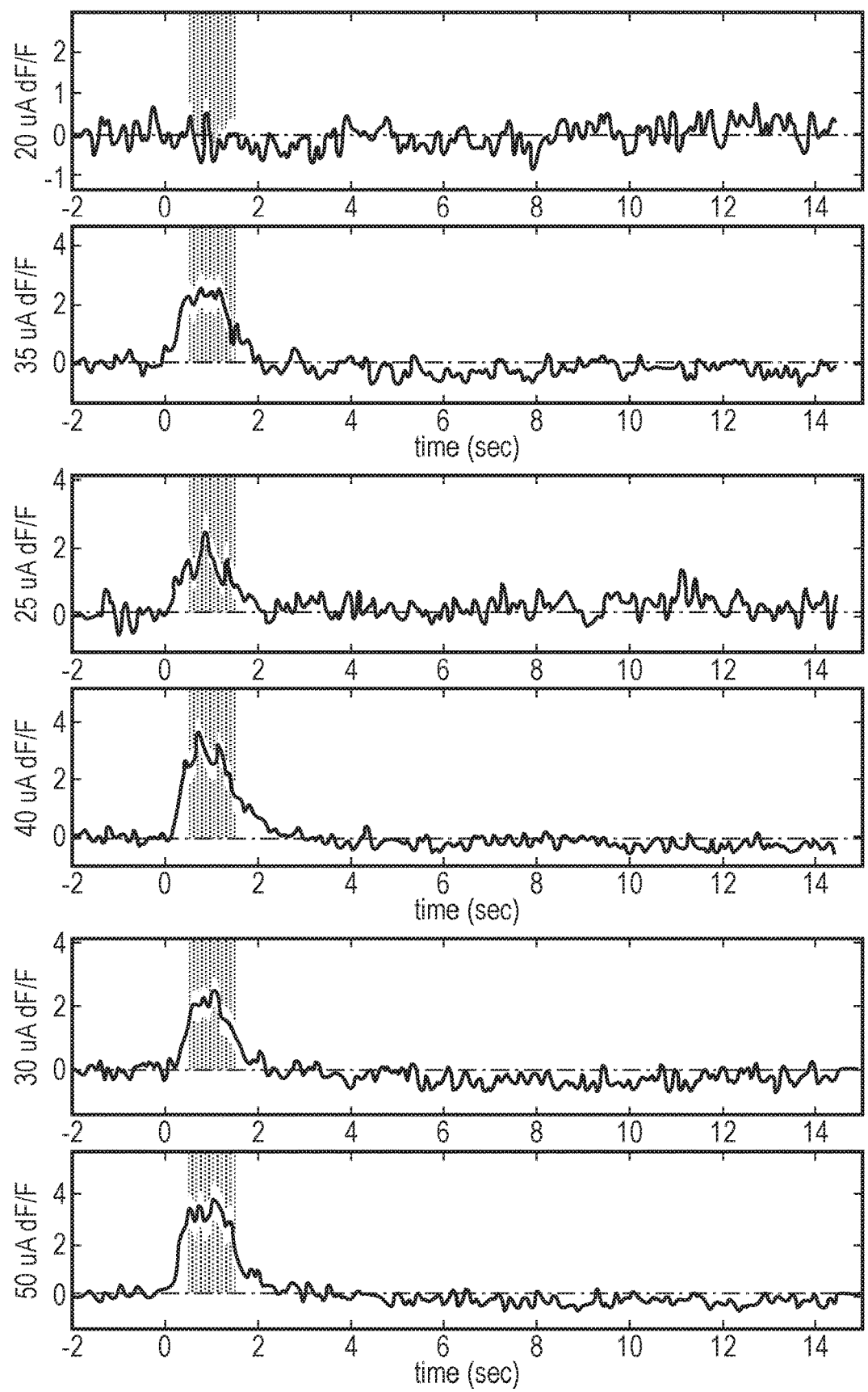
Figure 28:
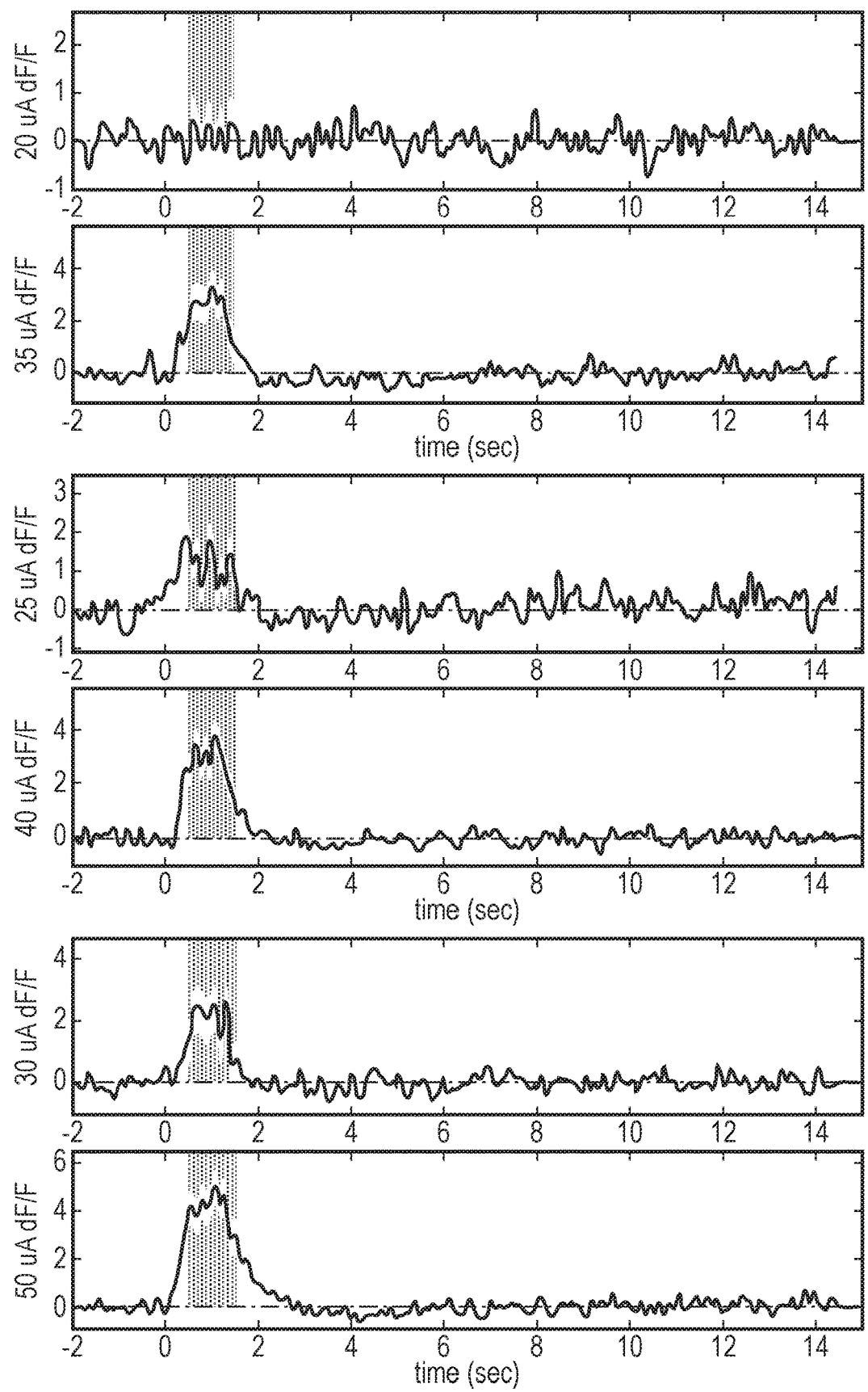
Figure 29:
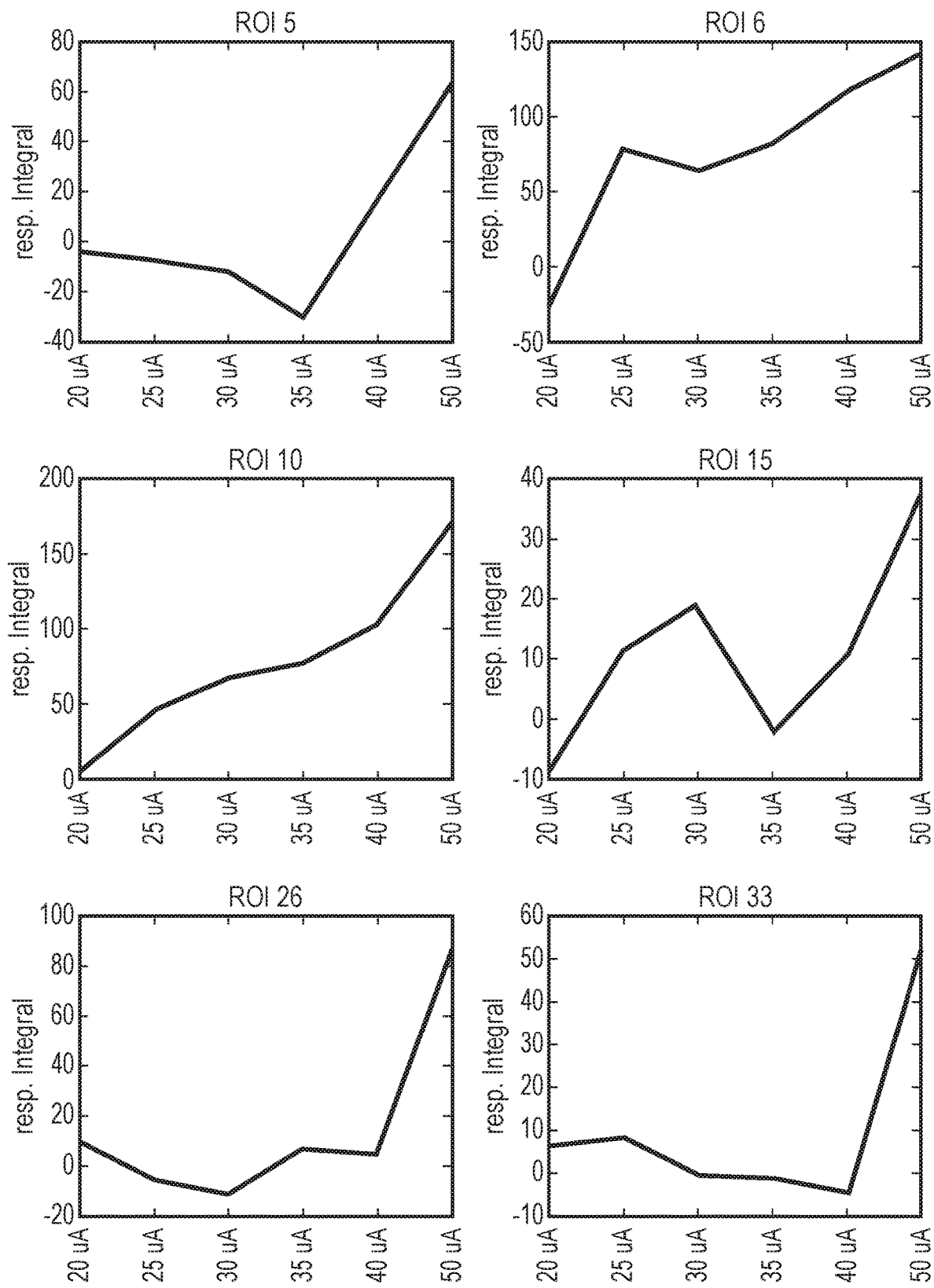
Figure 30:
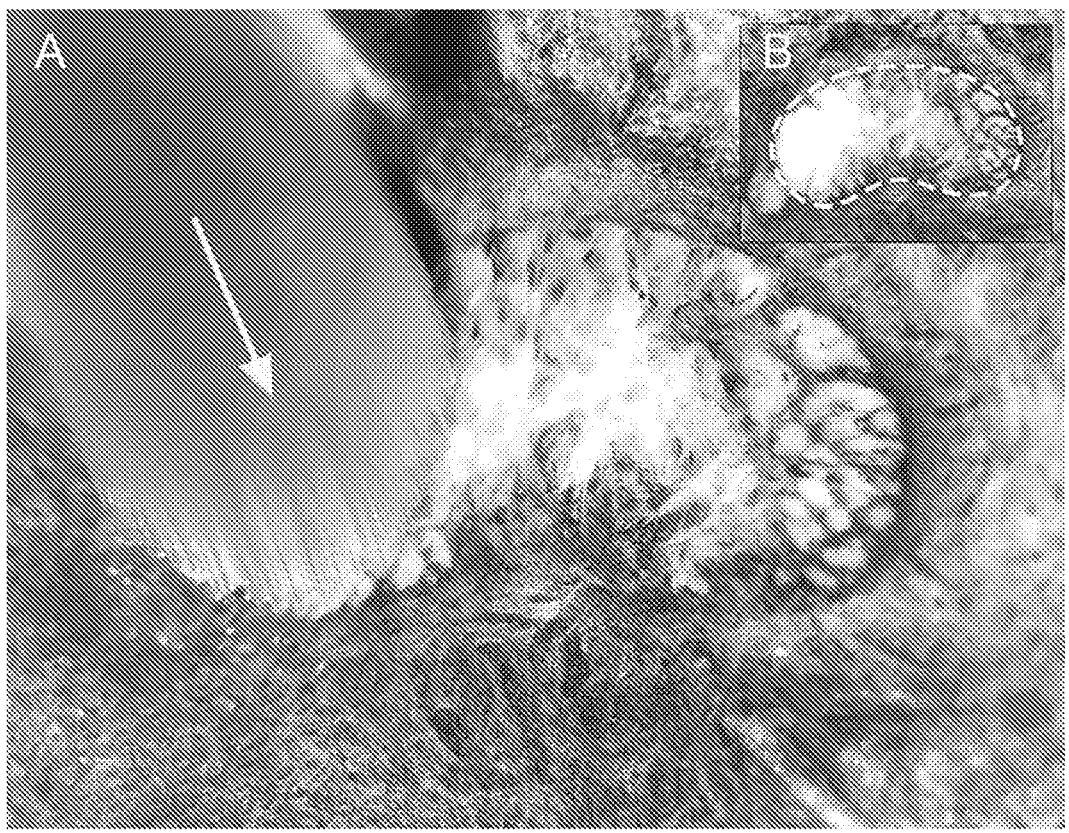
Figure 31:
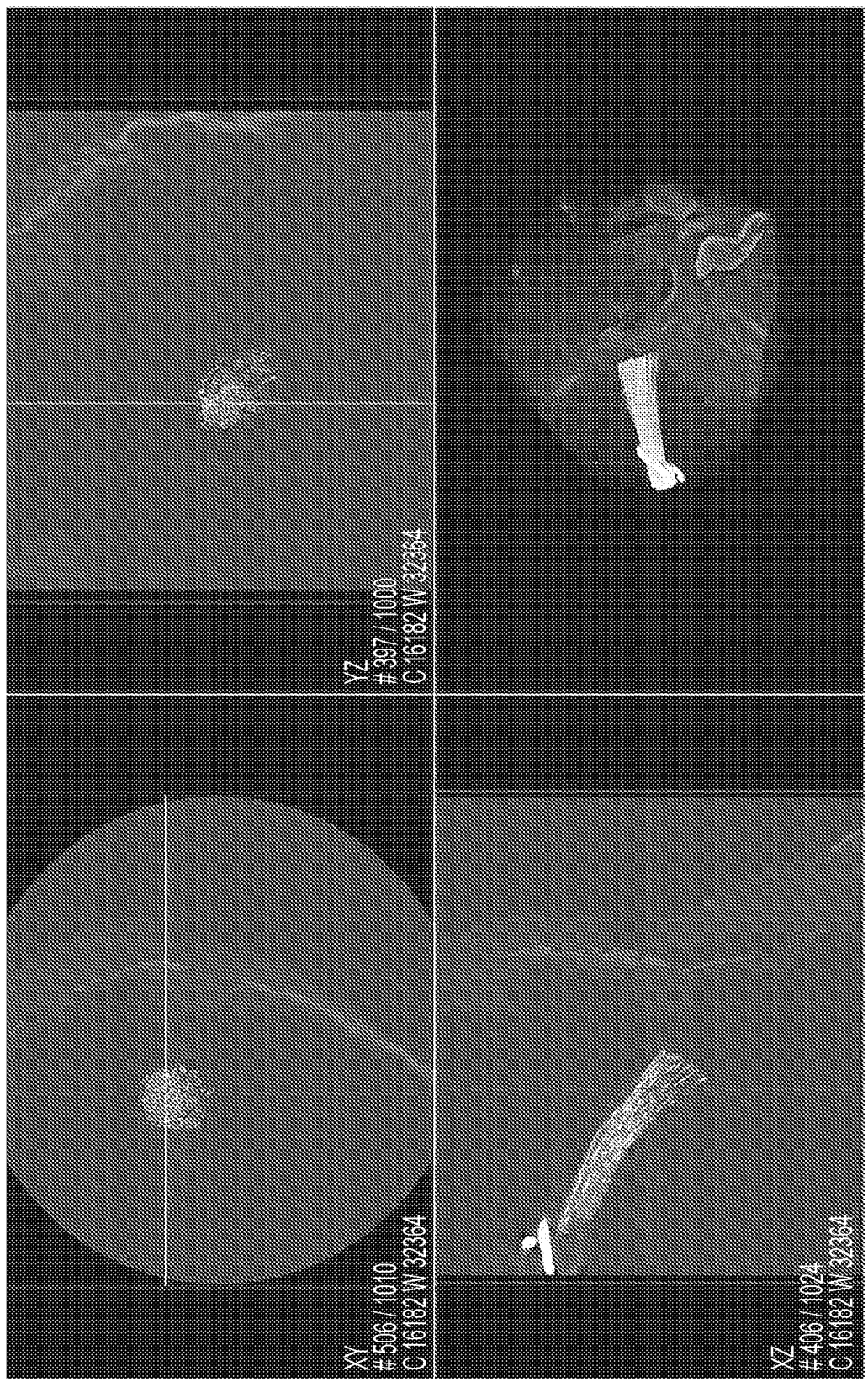
Figure 32:
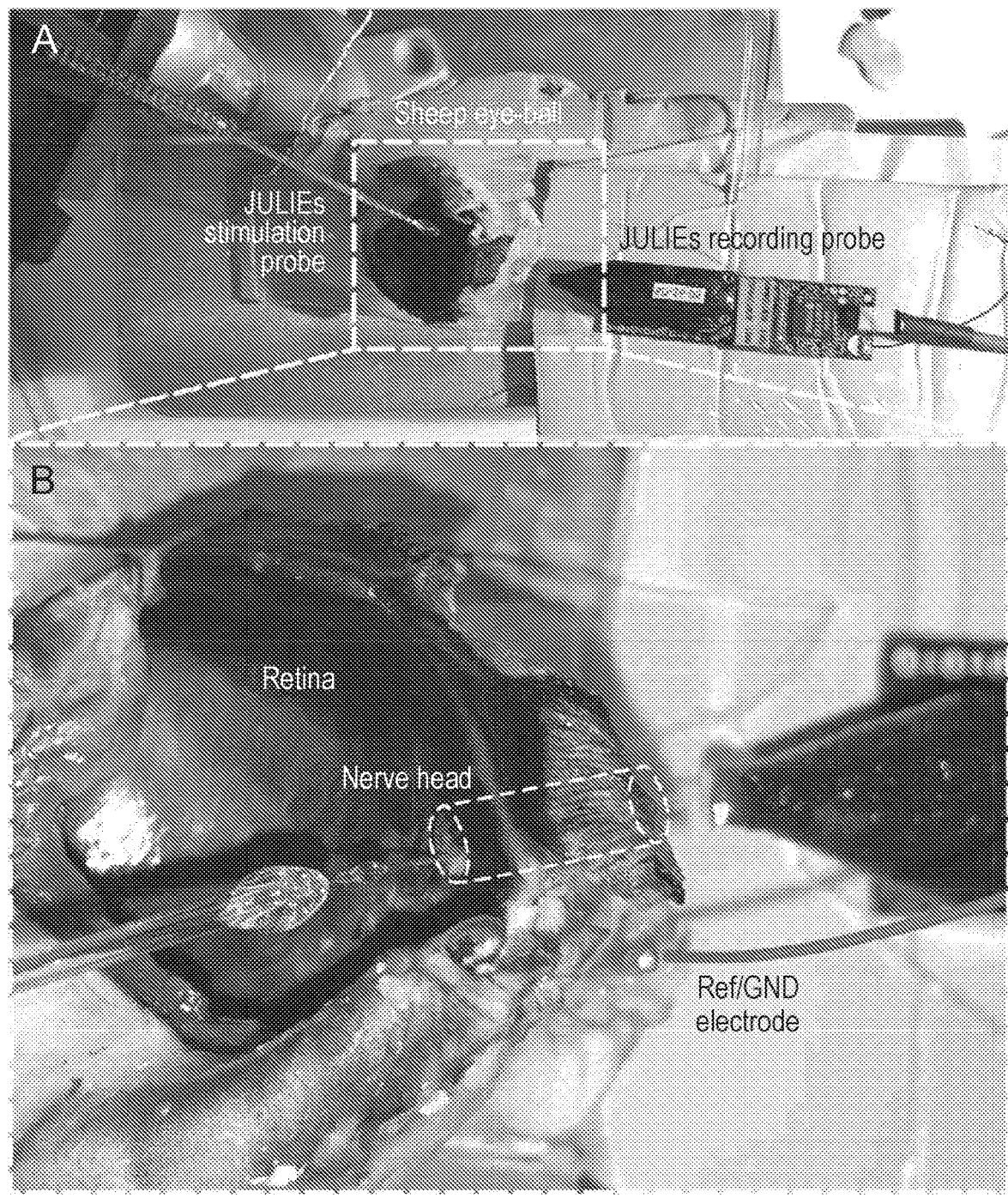
Figure 33:
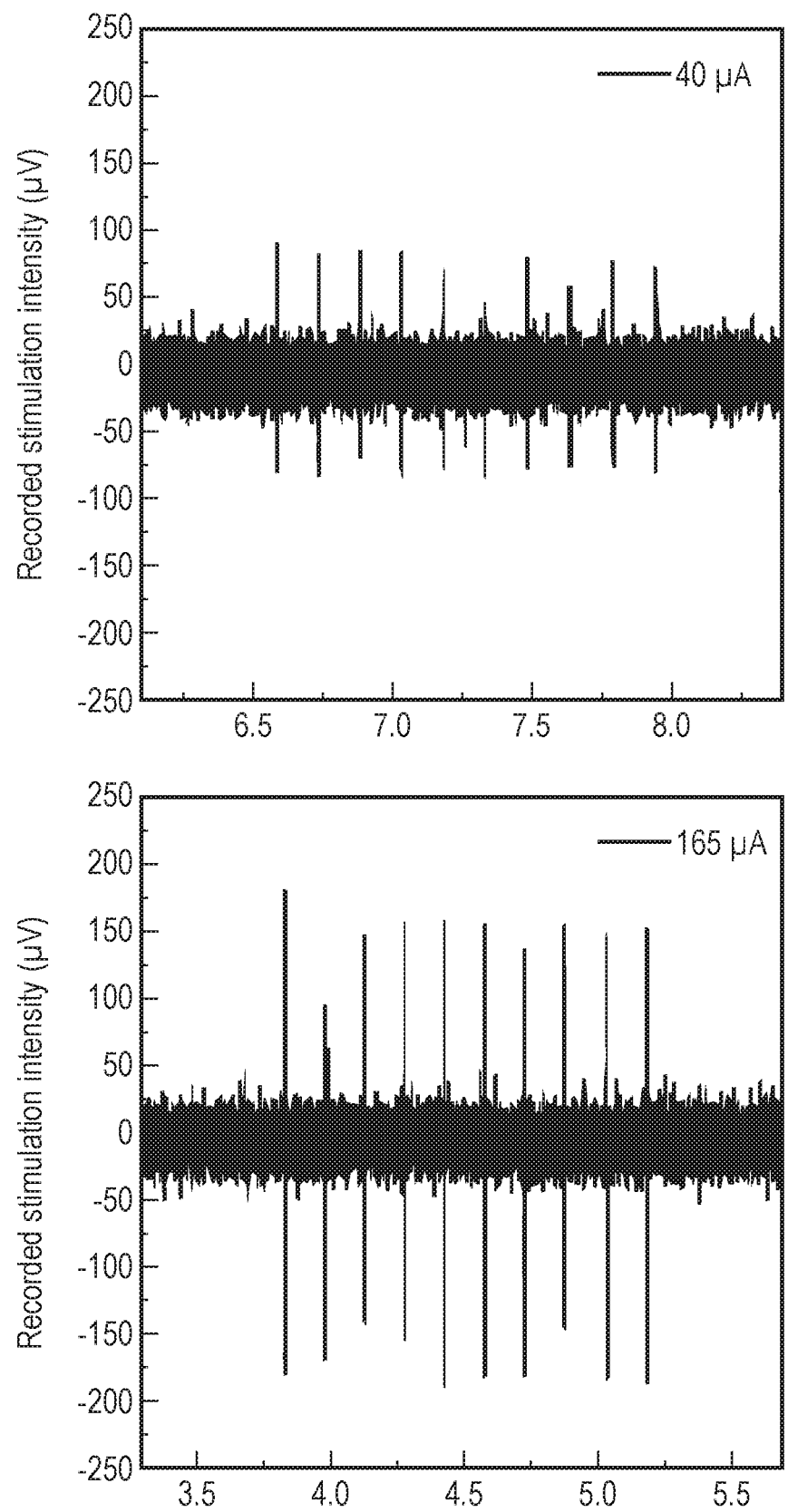

FIG. 10 schematically illustrates an example of an array of wire micro-electrodes of conducting material surrounded in insulating material with impedance reducing layers made of gold nano-structures deposited on the tips of the wires at the front and back ends, and an iridium oxide functionalization layer deposited on the gold nano-structures at the front end of the wires;

FIG. 11 shows an image of the wires before and after depositing the gold nano-structures;

FIG. 12 shows images of the bare metal core wire, the tip of the wire after depositing the gold nano-structures and the tip after depositing the iridium oxide functionalization layer on the gold nano-structures;

FIG. 13 is a graph showing how the impedance at the front end interface of the wires is reduced by including the layer of gold nano-structures;

FIGS. 14 and 15 compare signal amplitudes of neuronal recordings measured in a mouse brain using wires of a typical commercial probe and the micro-electrodes of FIG. 1 respectively;

FIG. 16 is a flow diagram illustrating a method of manufacturing the array of micro-electrodes;

FIG. 17 schematically illustrates an example of adjusting the relative positioning of the micro-electrodes in the array using a magnetic field;

FIG. 18 is an image showing an example where the insulating sheathes of the electrodes are melted together to bond the wires together in the bundle;

FIG. 19 is a graph showing variation of the size of gold nano-structure bumps with electrodeposition time;

FIG. 20 shows an example of sharpened tips of the electrodes;

FIG. 21 shows an example where a recess is formed in the tips of the electrodes and the impedance reducing layer and functionalization layer are deposited on the inside of the recess;

FIG. 22 shows an example of an apparatus in which an integrated circuit is used to drive stimulation currents through at least a subset of the electrodes, and optionally read out and amplify the signals received from at least a subset of the electrodes;

FIG. 23 shows an example of providing at least one hollow-core channel in parallel to the micro-electrodes;

FIG. 24 shows an example of manufacturing electrodes partially embedded in cladding material along part of the length of the electrodes;

FIG. 25 shows in-vivo two-photon excitation microscopy images showing results of an experiment in which localised deep brain stimulation of neurons is performed in a mouse using the micro-electrode array;

FIGS. 26 to 28 illustrate the response to different magnitudes of stimulation current for three respective stimulation sites in the experiment of FIG. 25;

FIG. 29 summarises the response to different magnitudes of stimulation current for a six stimulation sites in the experiment of FIG. 25;

FIGS. 30 to 32 illustrate an in-vitro experiment in which the micro-electrode array is inserted into the ganglion cell axons in the optic disk of a sheep's eye and used to stimulate an observable response in the optic nerve; and FIG. 33 illustrates the recorded stimulation intensity detected in the optic nerve in the experiment of FIGS. 30 to 32.

A visual implant comprises an array of micro-electrodes which include at least two stimulation micro-electrodes. Each of the stimulation micro-electrodes comprises a core of conducting material, insulating material surrounding the core, and a layer of metal or metal oxide nano-structures deposited on tips of the micro-electrodes at a front end for interfacing with a target site for visual stimulation. The visual implant also includes an integrated circuit to control a pattern of stimulation current driven through the array of micro-electrodes.

A problem with existing techniques for visual stimulation has been that the electrodes used typically have a relatively high impedance at the interface between the electrode and the tissue being stimulated, and so this has often necessitated use of relatively high currents and additional circuitry for amplifying input signals to generate the stimulation currents. A disadvantage of using higher currents is that this may cause more tissue damage, and also the additional amplification required may increase the power consumption of the device.

In contrast, the visual implant discussed in the examples below has a layer of metal or metal oxide nano-structures deposited on tips of the micro-electrodes at the front end for interfacing with the stimulation target site. This helps to reduce impedance at the front end of the micro-electrodes, hence reducing the currents required and the amount of amplification of the stimulation currents needed, helping to reduce the likelihood of tissue damage and reduce power consumption of the implant. Hence, this implant can act as a more effective tool for supporting research into the way in which visual stimulation by applying stimulation currents from electrodes is perceived in terms of an image by the brain, enabling better research into the detailed understanding of how the visual system functions. Also, such a visual implant can also be more effective for restoring vision in individuals with sensory loss. If the implant is used as a research tool for example, then this could be used to drive the electrodes with certain test patterns of stimulation current and then the effect of each test pattern can be studied, either by asking a human individual to describe the visual sensations experienced when certain patterns of stimulation current are applied, or by using a second implant to sense changes in a human or animal's brain caused by applying particular patterns of stimulation current.

The micro-electrodes may have a diameter at the micron scale. More particularly the micro-electrodes may have a diameter less than or equal to 30 µm; or less than or equal to 25 µm, or less than or equal to 20 µm, or less than or equal to 15 µm, or less than or equal to 10 µm. Given the micron scale of the electrodes, this means that an implant may have much higher channel count compared to current techniques which use wider electrodes. This is useful as given the large number of photosensitive cells involved in vision then practical visual implants may need to be able to stimulate in the order of 10,000 or 100,000 cells or axons. This is typically not practical in existing techniques. Hence, by using extremely narrow micro-electrodes formed using a conducting core and an insulating surrounding, this can provide a much improved platform for enabling better research into the visual sensation in humans or animals and eventually better implants for sight restoration. Another advantage of using narrower micro-electrodes is that, because the current at each location stimulated by an individual electrode is much lower, and heating of tissue is proportional to the square of the current, the amount of tissue damage can be much less than if fewer electrodes with larger widths and larger currents were used.

In some examples the number of stimulation micro-electrodes provided may be greater than 100; or greater than 1000; or greater than 10000; or greater than 100000.

As well as the layer of metal or metal oxide nano-structures on the tips of the micro-electrodes at the front end, which may help to reduce the interface impedance, the at least two stimulation micro-electrodes may also have a connection layer of metal nano-structures deposited on tips of the micro-electrode at a back end for interfacing with the integrated circuit. This may help reduce resistance at the interface between the electrodes and the integrated circuit again reducing losses and hence reducing the amount of amplification required which saves power. The compressible nature of the layer of nano-structures at the back end can also be helpful for improving bonding with the integrated circuit, as the nano-structures when pushed against bumps on the integrated circuit may squash to provide a tight coupling and can squeeze into gaps more easily than solid conducting material.

The nano-structures at the front end may be made from a range of materials but in one example may comprise nano-structures made of a noble metal. For example the noble metal may be gold. Similarly the nano-structures at the back end could also be made of gold or other noble metals.

In some cases, the stimulation micro-electrodes could also comprise a functionalisation layer deposited on the layer of metal or metal oxide nano-structures at the front end. The functionalisation layer may be made from a range of materials such as inorganic materials such as metal oxides, e.g. iridium oxide or copper oxide, or other substances such as DNA, graphene, carbon nanotubes, antibodies, aptamers, enzymes etc. The functionalisation layer may support improved delivery of stimulation current through the micro-electrodes (e.g. a layer of iridium oxide may boost charge capacity to improve current injection), and/or may support other diagnostic or sensing functions, e.g. targeting particular biomarkers.

Various insulators could be used to surround the conducting core of the micro-electrodes, but in one example the insulating material surrounding the core in the stimulation micro-electrodes may be glass. Glass-unsheathed metal micro-electrodes can represent an ideal platform for high channel count interfacing with elements of the visual pathway as this provides a biocompatible and aseptic material which permits formation of mechanically flexible electrodes, which can be advantageous to reduce tissue damage when the electrodes are inserted. In one example, the micro-electrodes may comprise "microwires" or Taylor-Ulitovsky wires, formed using the Taylor-Ulitovsky method. The Taylor-Ulitovsky method is a technique for forming conducting wires surrounded by glass, with extremely narrow widths. It has been found that Taylor-Ulitovsky wires have extremely low impedance when treated with the layer of nano-structures on the front end tips providing an extremely versatile, biocompatible and precision instrument for exploring the phenomenon of vision by supporting experimental research into visual stimulation and implementing visual implants for visual sight restoration. Also, Taylor-Ulitovsky wires have extremely smooth sides, reducing the likelihood of surface roughness causing tissue damage as the electrodes are inserted or removed.

In one example, the tips of the micro-electrodes at the front end may have a polished angled tip surface with a sharpened point, and the at least two stimulation micro-electrodes may have the nano-structures formed on the angled tip surface. The angled tip helps facilitate better insertion into the sample, reducing the amount of tissue damage.

The integrated circuit for driving the stimulation current through the micro-electrodes can be implemented in different ways. However in one example the integrated circuit may comprise a pixel display driver comprising a number of pixel units for driving respective pixels of a display. For example the pixel display driver may be an integrated circuit for driving an LED, organic LED (OLED), or micro-LED (mLED) display. The pixel display driver may be a commercially available existing form of driver used with existing types of pixel display. For example integrated circuit may be the same type of the circuit that would be included with LED, OLED or mLED displays, but without the actual display unit. This type of pixel display driver may already have a number of pixel units which have amplifiers which can be selectively driven with current and through which the current can then be supplied to the micro-electrodes. Hence, by reusing commercially available integrated circuits this can reduce the cost of developing the visual implant, making it cheaper to develop a suitable research platform for exploring the visual stimulation or an eye implant. Alternatively bespoke integrated circuits could be designed with different designs for each pixel unit.

The bonding between individual micro-electrodes and corresponding pixel units of the pixel display driver could be done with individual metallic/conducting bonds being formed between the micro-electrodes and the individual pixel unit. However, when the channel count is particularly high, and given the small size of the micro-electrodes, in some cases there may not be a specific bonded connection formed in the manufacturing process. Instead, in one example the back ends of the micro-electrodes can simply be pushed up against the pixel units of the integrated circuit and the connection between particular pixel units and individual electrodes can simply be formed by the contact between the two. The back end metal nano-structures discussed above can be particularly helpful in allowing such connections to be formed, since the nano-structure of the back end bumps can be squashed on impact with the corresponding pixel unit to form a better connection. This is discussed in more detail below.

In other examples, the integrated circuit could also include some pixel units which measure currents detected through some of the electrodes. In this case, in addition to pixel units for driving currents there could also be a separate pixel unit with amplification for reading out current, similar to the pixel units that may be provided within a CMOS imaging sensor for example.

In one example, the integrated circuit may perform simultaneous driving of currents through stimulation micro-electrodes of the array arranged in a two dimensional pattern. That is, rather than sequential raster-scanning across the two-dimensional array in a series of one dimensional lines, the integrated circuit may be designed to simultaneously apply current through different micro-electrodes extending over two dimensions simultaneously. A simultaneous driving mode can be useful for a visual implant, because raster-scanning sequentially may cause synchronicity problems in the brain.

In some examples, an arbitrarily selected pattern of stimulation current may be selected to be driven through the array of micro-electrodes. For example, for running a particular test or research experiment, then certain stimulation patterns could be devised and communicated to the integrated circuit (or generated within the integrated circuit itself), and then such currents could be applied by the stimulation electrodes, and feedback can be gathered on the effects of such stimulation, either by asking the individual in which the implant is implanted for a description of the visual sensations experienced, or by using other probes to measure brain function in response to the stimulation applied. This could then allow improved knowledge to be gained regarding the particular visual sensations elicited in response to certain stimuli, which could help for the subsequent development of visual implants for sight restoration.

However, in other examples the integrated circuit may receive image information indicative of a captured image and control the pattern of stimulation current based on the received image information. This could be useful for enabling the user's surroundings to be perceived visually by a blind or partially sighted user using the visual implant. In some examples, the image capture unit which captures the image may not be part of the implant itself. Instead, the implant may comprise a wireless communication unit which receives the image information from an external image capture device. This can reduce the complexity of the implant. For example, a head mounted image capture unit could be provided, which could be worn on the head of the user to capture an image approximately representing the viewpoint from the location of the user's eyes. The captured image can be used to derive the information to transmit to the integrated circuit within the implant. The integrated circuit in the implement can then drive a corresponding pattern of stimulation current based on the received image information.

In other examples, the implant itself may comprise an image capture unit to capture the captured image, and processing circuitry to process the captured image to generate the image information based on the captured image. This processing circuitry could in some cases be implemented on the same integrated circuit that drives the current through the electrodes, or alternatively could be on a separate integrated circuit. With this approach, the optical system and image sensor for capturing image may be provided within the implant to be positioned within the eye. This could be useful to reduce the inconvenience caused to the user by having to wear the head mounted image capture unit. Using an in-eye camera also means that alignment of the image capture unit is simpler to control, as effectively the muscles controlling the position of the eyeball may also reposition the image capture unit.

In some examples, the visual implant may include processing circuitry to detect features in the captured image indicated by the image information and to determine a pattern of stimulation current to be applied to the at least two stimulation micro-electrodes based on the detected features. For example the features detected could comprise edges, with a stimulation current then being applied to electrodes arranged in certain linear or curved patterns depending on the locations of the edges in the captured image. For example, this could provide a binary (on/off) approach where no attempt is made to recreate colours or shades, but edges in the perceived image are recreated in terms of stimulation currents in order to allow the user to perceive the boundaries of objects for example.

In other examples the features detected could comprise gradients, shades or colours and the stimulation could be modulated based on the detected features. For example, the processing circuitry could modulate at least one of the spatial position, frequency and intensity of the stimulation current applied to particular stimulation micro-electrodes based on the detected features. Hence this could help to recreate more complex forms of vision.

Again, providing processing circuitry of this form to derive patterns of stimulation from captured images can be useful in providing a platform for research enabling researchers to explore how to map features of captured images into stimulation currents to be applied and requesting feedback from the patient on what visual sensations have been experienced. Also, eventually visual implants can be provided to use the best identified approaches for mapping images into corresponding stimulation current patterns in order to provide an implant permitting restoration of visual function. The processing circuitry which detects the features in the captured image could be located either within the same implant that is to go into the patient, or as externally provided processing circuitry (for example within the same unit as the image capture unit in embodiments where the image capture takes place outside the body).

In some examples, the array of electrodes may comprise only the stimulation micro-electrodes so that all of the electrodes are for applying stimulation currents.

However, in other embodiments the array may also comprise at least one sensing micro-electrode and the integrated circuit may control supply of current to, or read out of voltage or current from, the at least one sensing micro-electrode for sensing a predetermined substance or condition. As the implant may provide electrodes which extend into portions of the visual system such as the optic disc, optic nerve or lateral geniculate nucleus (LGN) within the brain for example, this also provide an opportunity for diagnostic information to be derived from measurements taken by some of the electrodes. These measurements could be performed for the purpose of identifying responses to the stimulation current supplied by some of the electrodes, or could be for performing sensing independent of stimulation. For example, one cause of loss of sight may be diabetes and so it may be useful to use the implant for sensing the progression of diabetes or any biomarkers associated with this. For example, it may be useful to sense at least one of glucose or pH (protons, which may be a bio marker for glucose) and so the at least one sensing micro-electrode could comprise at least one glucose or pH sensing micro-electrodes. For example the sensing micro-electrodes provided for glucose or pH sensing may include, deposited on the layer of metal or metal oxide nano-structures at the front end of the electrodes, an additional functionalisation layer which may comprise at least one of iridium oxide, copper oxide or graphene, which can all assist with glucose or pH sensing. Another example can be to provide sensing micro-electrodes for sensing progression of Alzheimer's disease, based on amyloid beta detection in the retina. Also, it would be possible to detect glial fibrillary acidic protein (GFAP) in traumatic brain injuries and brain tumours (glioblastoma) by decorating the nano-structures with anti-GFAP antibody. Other types of functionalisation layer could include other inorganic compounds, enzymes, carbon nanotubes, aptamers, antibodies, or nucleic acid such as DNA or RNA.

Hence, if the array also includes sensing micro-electrodes then the integrated circuit may also comprise at least one read out circuit for detecting and amplifying a current measured through the at least one sensing micro-electrode. Also wireless communication circuitry may be provided to transmit detection results obtained from the at least one sensing micro-electrode to an external device. These read-outs can then be useful in diagnosing conditions in the patient. In some examples at least one micro-electrode of the array may function as both a stimulation micro-electrode and a sensing micro-electrode. For example sometimes current could be applied through an electrode and at other times current may be read out through the electrode. In this case, the corresponding element of the integrated circuit may require both drive capability and readout capability. Other examples may have a separation between the electrodes used for stimulation and the electrodes used for sensing. For a research tool, it can be useful to provide for both stimulation and sensing capability. For a practical visual implant, it may be preferred to increase the channel count available for stimulation by not providing any sensing micro-electrodes or by making each stimulation micro-electrode dual function (stimulation and sensing).

The implant may have a wireless power receiver for receiving power supplied by wireless communication from an external power source. This avoids the need to provide a complete power source within the implant itself, which would otherwise increase the size of the implant and make it harder to restore power once any battery within the implant has run out without costly operations. In some cases, all of the power required by the implant may be received from external sources by the wireless communication. For example any known radio frequency power technique currently used for medical implants can be used. Alternatively, in some cases the visual implant could have a battery or other form of charge storage, but by providing means for supplying power to charge the battery from a remote source through wireless communication this means that reduces the chance an implant implanted into a patient needs to be replace due to batteries running out.

Given the extremely large number of photosensitive cells involved in natural sight for high detailed vision stimulation for sight restoration may require stimulation of a significant fraction of its elements, in the order of 10000 s or 100000 s cells or axons. Interaction in a compatible manner with the visual pathways to elicit useful and reproducible phosphenes also requires the understanding of large-scale computation performed by its elements. To date, implantable retinal microelectronic devices offer several hundred stimulation/recording sites, are not readily scalable or have no multiple sensing modalities, are prone to infection and require complex surgical and non-implantation procedures. High channel-count visual prosthetic devices described below combine penetrating metal ultramicroelectrodes (UMEs) arrays with very large scale integrated (VLSI) circuitry to record activity and stimulation. By combining micron-sized metal microwire arrays by bonding with pixelated integrated circuits, a versatile, biocompatible and precision instrument is developed. Protruding microwire arrays can be up to a several centimetre long, are mechanically flexible and can be readily inserted into healthy ROIs in the optic disk to interface with the ganglion cell axons.

Given the lack of detailed understanding of how retinal function contributes to the formation of an image, the focus here is on the ganglion cell axons which collect information from the within the retinal layer and transport it as electrical/biochemical information along the visual pathway to form the visual sensations or phosphenes.

Glass-ensheathed metal microelectrodes represent an ideal platform for high channel count and biocompatible interfacing with the numerous elements of the visual pathway. Sharpened microwires can access ganglion cell axons (GCAs) through the optic disk contained within the optical nerve causing un-detectable damage to the extracellular matrix or the blood brain barrier.

Here, a prosthetic device is developed from the combination of sharpened metal microelectrodes as interface between electronics and tissue with arrays of amplifiers and/or potentiostats. The latter are drivers for information retrieval (recording) and charge injection (stimulation) into the nerve bundles. By stimulation of a subset of GCAs, visual sensations could be evoked in the form of contours and colours which form the basis of useful sight.

Given the micron scale dimensions of the microwires and increasingly high channel count of VLSI electronics, a sensory function restoration apparatus can contain several tens of thousands of contacts (pixels) for high granularity stimulation without causing damage to the tissue and blood-brain-barrier (BBB). Microwires satisfy the electronic and mechanical requirements for stimulation and recording from neural tissue with single and multi-unit resolution. The prosthesis device may stimulate in a simultaneous manner, as opposed to sequential raster scan that might cause synchronicity problems downstream in the lateral geniculate nucleus (LGN) or visual cortex.

Also, given their chemically inert nature and availability of electronic components in the VLSIs, an array of electrochemical sensing elements can be integrated within the same apparatus, for e.g. glucose or pH detection for diagnostic purposes thus developing a versatile, scalable and highly precise prosthetic.

Given the aseptic requirements and volumetric limitations within the eye, two versions have been considered: a wireless enabled design where implanted UMEs receive patterned stimulation information on radio frequencies from a camera placed on a head-mount (see FIGS. 1-5) and a fully integrated bionic eye (FIGS. 6 and 7) with image acquisition and processing contained within the eye.

FIG. 1 schematically illustrates a first example of an implant 2 for providing stimulation of a portion of the visual system. The target site selected for visual stimulation may vary and could for example be the retina, the optic disc (the portion of the eye at which the ganglion nerve axons leave the eye and become the optic nerve), the optic nerve itself, or a portion of the brain at which signals from the optic nerve are received, for example the LGN, which is the relay centre in the thalamus for the visual pathway. In particular, stimulation of ganglion cell axons within the optic disc can be particularly effective because this part of the visual system is easily accessible and the axons within the optic disc are orientated in a parallel arrangement similar to the arrangement of the micro-electrode array, making the interface more effective.

As shown in FIG. 1, the implant 2 includes a micro-electrode array 4 which includes a number of electrodes which protrude outside the housing of the implant so that they can be injected into the target site of the visual system. A drive/read out integrated circuit 6 is provided for controlling the pattern of stimulation current driven through selected electrodes of the array 4. Optionally, the integrated circuit may also provide read out functionality for reading currents measured through the electrodes.

A wireless power receiver 8 is provided for receiving power supplied wirelessly by radio frequency communication from a wireless power supply unit 20 provided separately from the visual implant 2. The wireless power supply unit 20 includes a power source 22, such as a battery or ambient energy harvesting unit (e.g. a solar cell), and a wireless power transmitter 24 for transmitting energy wirelessly to the receiver 8 in the implant 2. Any known technique for inductive or radio frequency energy transfer can be used. The wireless power supply unit could, for example, be worn on the user's head or body so as to be in proximity to the visual implant 2.

The visual implant 2 also includes a wireless data receiver/transmitter 10 for communicating data by wireless communication with a head mounted image capture device 30. The wireless communication may be performed by any wireless protocol (e.g. Wifi®, Bluetooth®, etc.). The image capture device 30 includes an image capture unit 32 which includes an optical system and imaging sensor for capturing an image, a processor 34 for processing the captured image to generate a pattern of electrical stimulation to be applied to the micro-electrode array 4 within the visual implant 2, and a wireless data transmitter/receiver 36 for transmitting image information to the implant 2. The image information indicates the pattern of stimulation to be applied based on the captured image. The image information received from the image capture device 30 by the wireless data receiver 10 in the visual implant controls the drive/readout integrated circuit 6 to apply the specified pattern of stimulation current to electrodes of the array 4. The stimulation currents may be applied simultaneously to a two-dimensional pattern of electrodes, rather than using a sequential raster scan. In alternative examples the processor 34 for deriving the pattern of electrical stimulation from the captured image could be provided within the visual implant between the wireless data receiver 10 and drive integrated circuit 6, instead of being in the head mounted image capture device 30. Also in some examples the wireless power supply unit 20 and image capture device 30 could be combined into one device.

FIGS. 2 and 3 show an example of the micro-electrode array in more detail. The individual micro-electrodes 104 are held within a block 105 of spacer material which extends along part of the length of each electrode. An example of a method for embedding the electrodes in the spacer material is described with respect to FIG. 24 below. FIGS. 2 and 3 show different views of the micro-electrode array 4.

FIGS. 4 and 5 show an example of the implant embedded within the fundus of an eye, with the micro-electrodes 104 of the array 4 protruding into the optic disc to interface with ganglion cell axons in the optic nerve. The sharpened penetrating electrodes 104 are bonded to the integrated circuit 6, which may for example be VLSI (very large scale integration) circuitry similar to that used in an OLED display. In this example, the processing circuitry 34 for mapping received image information to a pattern of stimulation currents is also included within the implant, but this could also be provided within a separate head mounted image capture device. The wireless power receiver 8 and wireless data receiver 10 are also shown. Hence, in this example, processed image information is transmitted wirelessly from a head mounted acquisition system 30 to the implant.

Figure 6:
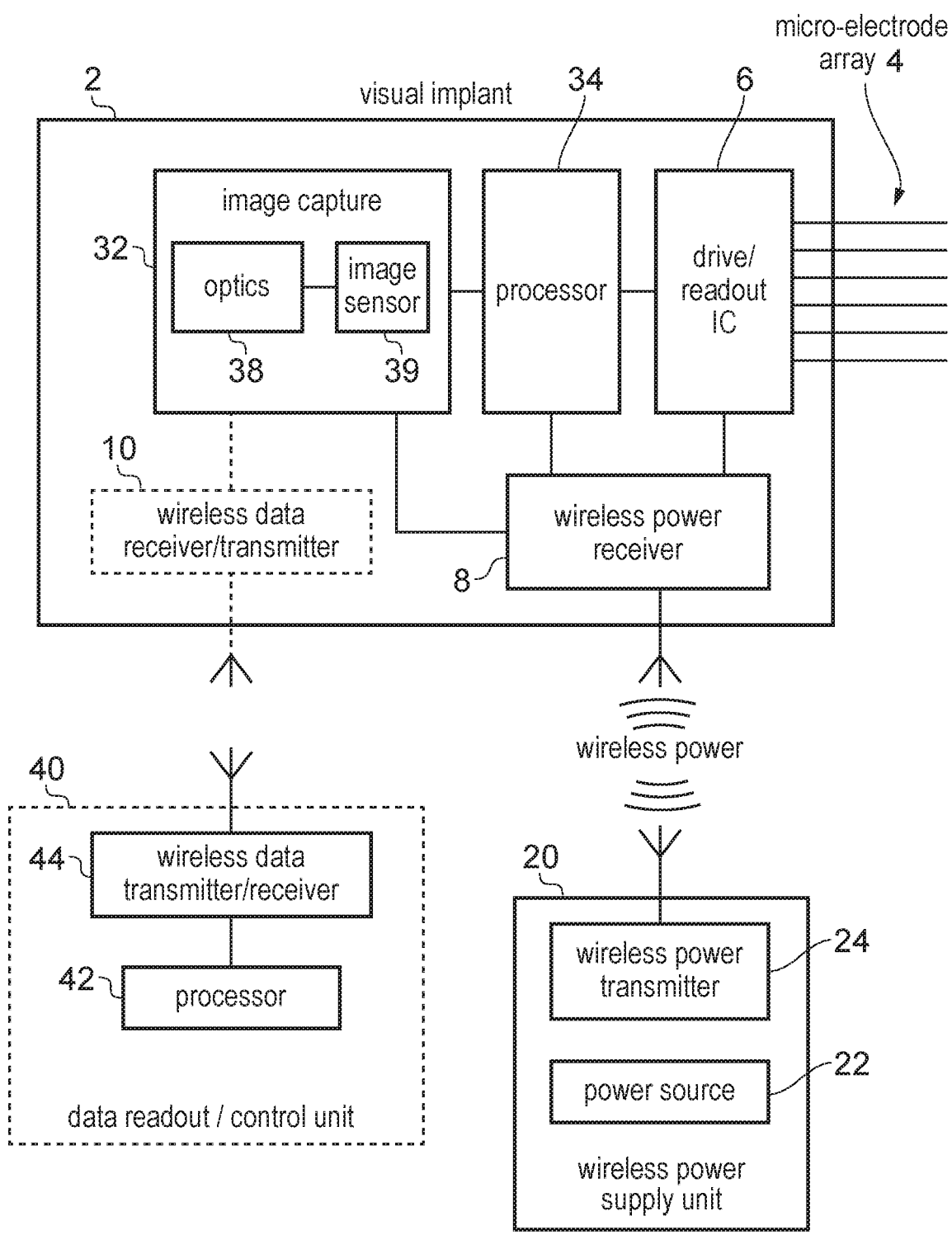
FIG. 6 shows a second example of a visual implant comprising an image capture device within the portion to be implanted in the eye.

FIG. 6 shows a second example of the implant 2, which in this example includes the image capture unit 32 and processor 34 within the same device as the drive/read out integrated circuit 6, micro-electrode array 4 and wireless power receiver 8. Hence, imaging optics 38 and an imaging sensor 39 can be included within the visual implant. The wireless power supply unit 20 is the same as in FIG. 1. With this example, the wireless data receiver/transmitter 10 is not essential as the image can be captured within the implant itself. However it may still be desirable to provide the wireless data receiver/transmitter 10 for communicating with a separate data readout/control unit 40. For example, if the integrated circuit 6 is able to make current measurements through the electrode array 4, it may be desirable to transmit values derived from the readouts by the processor 34 to the remote data readout/control unit 40 so that these measurements can be analysed. Also, for control purposes of the implant, it may be possible to set certain configuration settings of the implant through a remote control unit 40 by wirelessly transmitting control signals to be received by the receiver 10 within the implant 2. The data readout/control unit 40 may have a processor 42 and a wireless data transmitter receiver 44 similar to the head mounted image capture device 30 of FIG. 1 but may not have the image capture unit 32.

Figure 7:
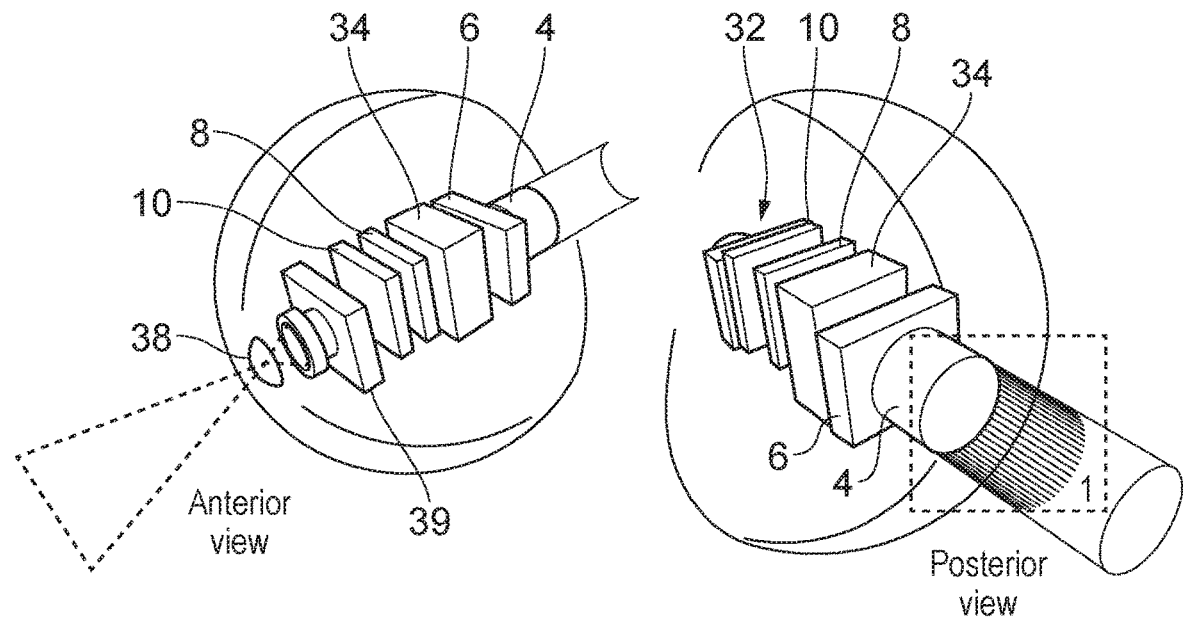
FIG. 7 shows anterior and posterior views of the implant implanted within the eye for stimulation of the optic disc.
Figure 7:
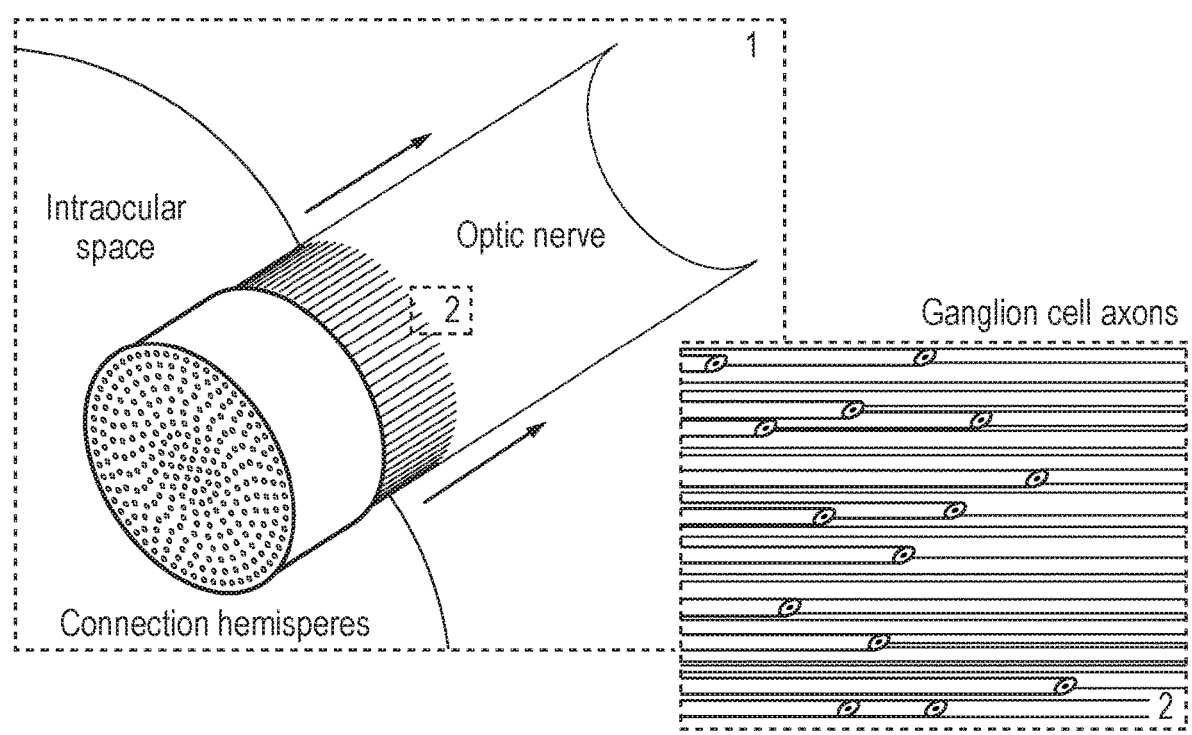

FIG. 7 shows the implant of FIG. 6 in use when embedded within the eye. With a fully integrated implant containing image acquisition and processing hardware combined with power banks and the VLSI drive integrated circuit 6 for driving stimulation currents through the electrodes, this means that the existing muscles for positioning the eyeball in order to look in a certain direction can be reused for controlling the orientation of the imaging sensor and optics to simplify use of the implants by the patient. As shown in the lower part of FIG. 7, the micro wire arrays are placed by penetration into the optic disc in parallel with the ganglion cell axons facing recording or stimulation sites towards high processing areas of the brain such as the LGN or the posterior part of the head. The anatomical structure of the ganglion cell axons shown in FIG. 7 (with a number of elongate cells arranged side by side in parallel) matches well with the parallel arrangement of the electrodes in the array 4, which provides an efficient interface.

Figure 8:
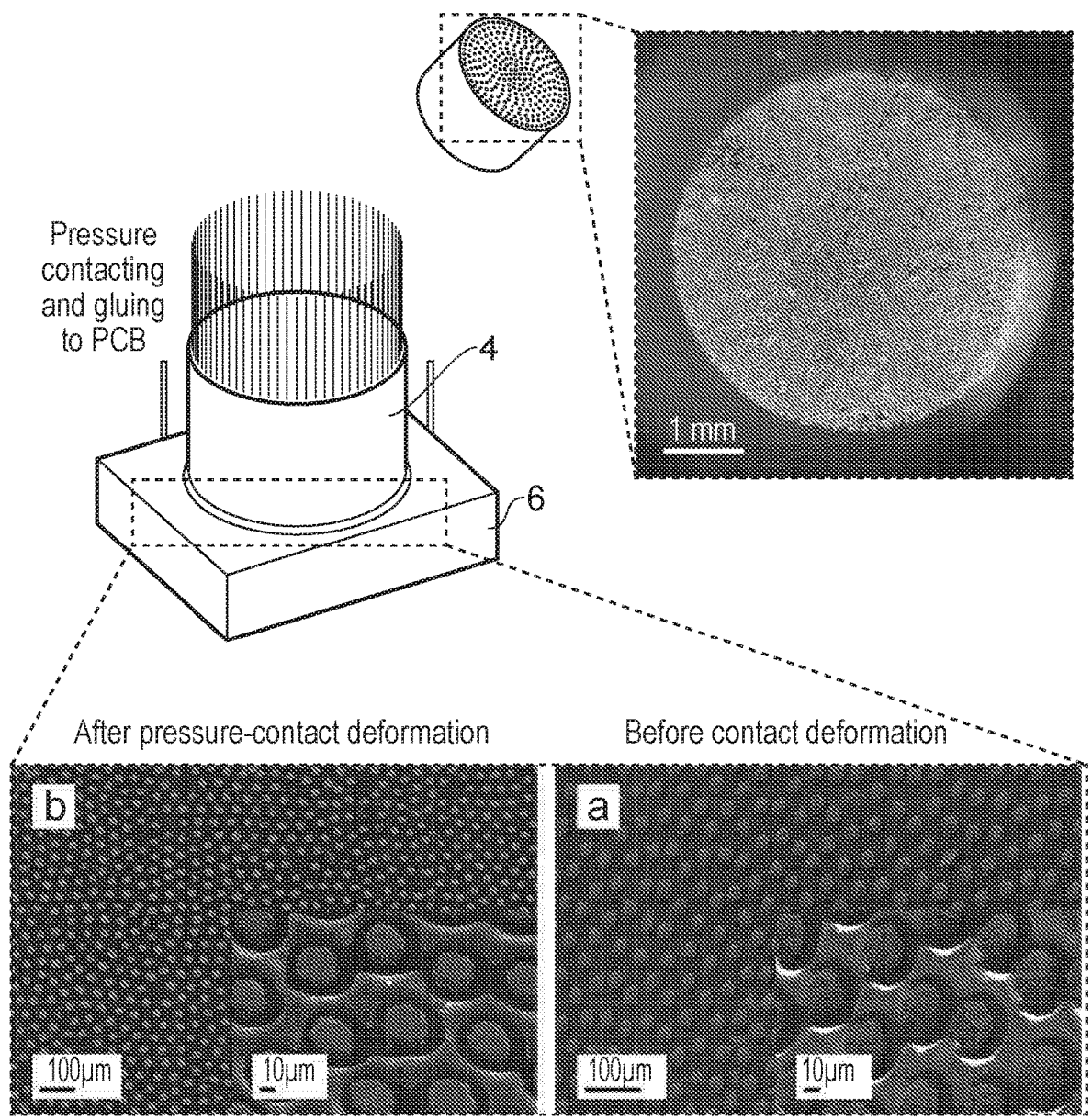
FIG. 8 shows optic microscopy images of the micro-electrode array.
Figure 9:
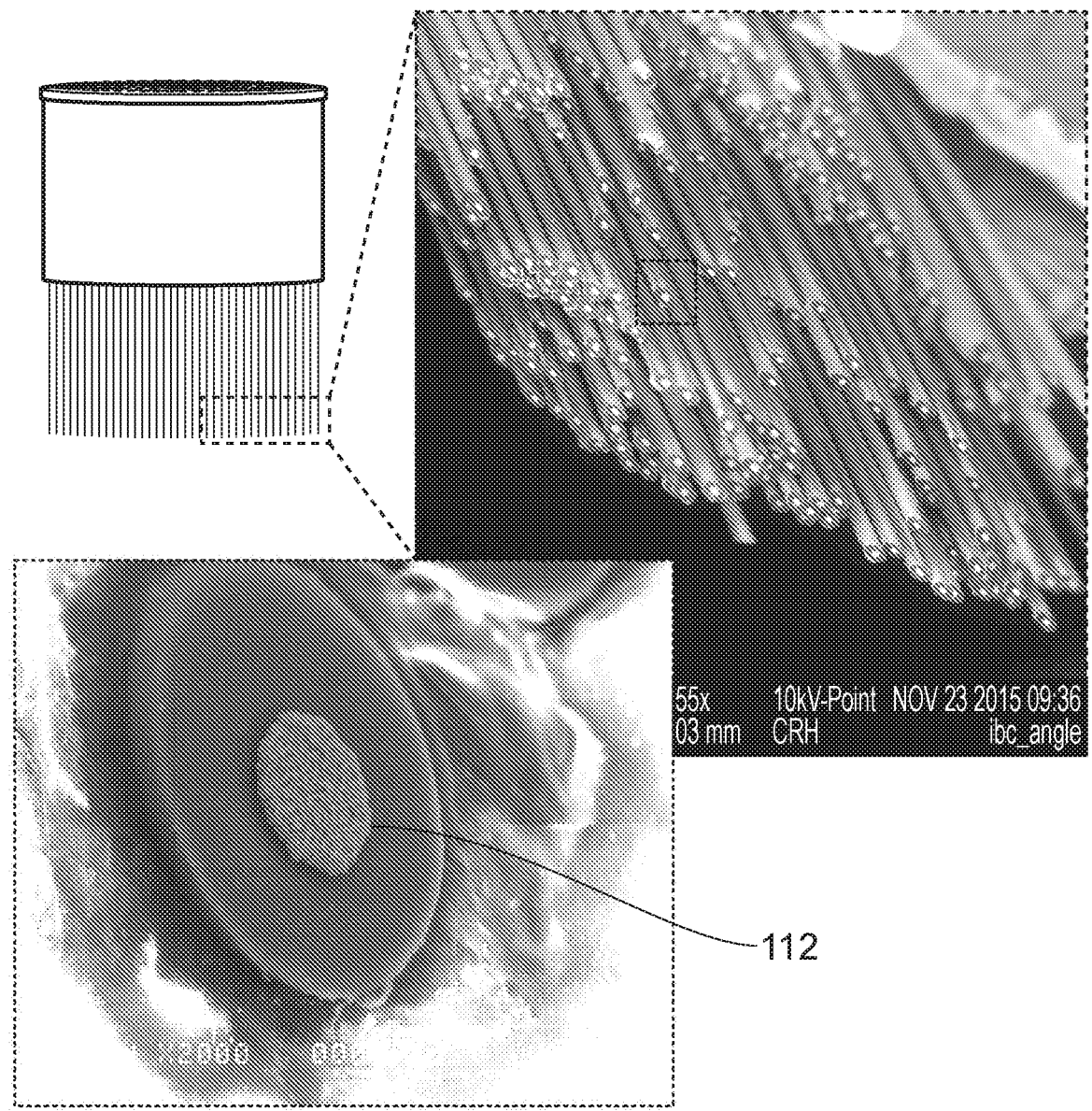
FIG. 9 illustrates angle-polished tips of the micro-electrode.

FIG. 8 shows the bonding of the VSLI circuitry 6 to the micro-electrode array 4 by the deformation of nano-structured gold hemisphere contacts at the back end of the electrodes. Optical microscopy images of a micro wire array are shown with the nano-structure gold contact points. FIG. 9 shows how at the front end the tips of the micro wires are polished to form an angled surface with a sharpened point and then the polished metallic cores are electrochemically modified by the deposition of a layer of nano-structures 112. In this example, the nano-structures are made of gold, but they could also be formed of other metals or metal oxides. This deposition of the nano-gold layer is followed by a deposition of a redox reversible material for charge capacity improvement, such as iridium oxide. Also a secondary sensing modality specific to a detection analyte, such as glucose, may also be provided.

FIG. 10 shows an example of a portion of the array 4 of micro-electrodes (wire electrodes) of the visual implant 2 in more detail. A number of electrodes 104 are arranged in a bundle with the electrodes 104 arranged alongside each other (for example the wire electrodes may be arranged parallel to each other or nearly parallel). The wires could be arranged in the bundle in a regular pattern (such as a square/rectangular lattice or stack arrangement, or a hexagonal packed arrangement), or in an irregular pattern. Each wire electrode 104 includes a core 106 made of a conducting material (e.g. a metal or alloy) surrounded by an insulating material 108. The electrodes 104 are ultramicroelectrodes (UMEs) having a diameter less than or equal to 30 μm. In this example the metal core 6 is made of gold, but other examples of conducting materials which could be used include copper, silver, gold, iron, platinum, lead or other metals, as well as crystalline or amorphous alloy compositions such as brass, bronze, platinum-iridium, lead-silver and magnetic alloys such as FeSiB. In this example, the insulating material 8 is glass, but other examples could use plastics or other insulators.

The electrodes 104 have a front end for interfacing with the target site for visual stimulation. The target site could be a site within the eye fundus, such as the retina or optic disc, or could be a site of the visual system outside the eye fundus, such as the optic nerve or the lateral geniculate nucleus (LGN, also known as lateral geniculate body). The electrodes 104 also have a back end for interfacing with the integrated circuit which drives the stimulus currents and/or receives signals measured from the target site. At the front end, the wire electrodes 104 each have an impedance reducing layer of gold nano-structures deposited on the tips of the wire electrodes, and an iridium oxide (IrOx) functionalisation layer comprising a layer of iridium oxide nano-structures deposited on top of the gold nano-structures. At the back end, the tips of the wire electrodes have a connection layer for connecting to the integrated circuit. The connection layer in this example is also made of gold nano-structures, but the back end does not have the additional functionalization layer.

FIG. 11 shows an image of the back end before hemisphere deposition (upper image) and of the gold nano-structure hemispheres formed on the back ends of the wires (lower image). Each individual single crystal of the hemisphere may have a unit size in the nanometre scale, e.g. smaller than 300, 100 or 50 nm for example. On the other hand, the overall hemisphere of nano-structures on the back-end may have a width at the micrometre scale, e.g. around 10-20 μm in this example. As can be seen from FIG. 11, the hemisphere may extend over the insulating sheath of the wires as well as the core material on the back-end to facilitate contact with the integrated circuit providing the electronics for reading out signals from the electrodes. The hemispheres at the front end may be narrower and extend over a smaller percentage of the wire tip surface than the back end hemispheres (e.g. see the front end image of FIG. 9). It will be appreciated that the gold-nanostructure layers formed at the front and back ends of the wire electrodes need not be perfectly hemispherical—in general any mound or bump formed on the tip of the wire electrodes may be sufficient.

FIG. 12 shows images illustrating the various layers deposited at the tips of the wire electrodes. The left hand image of FIG. 12 shows the bare polished metal core prior to depositing either of the layers onto the tip of the wire. The middle image shows the electrode after depositing the gold nano-structure layer. The layer of gold nanostructures has a flaky consistency, providing a large surface area for charge transfer which helps to reduce the impedance at the tips of the wire. The right hand image of FIG. 12 shows an image of the wire electrode after depositing the iridium oxide layer on top of the gold nano-structure layer. The iridium oxide layer has a spongey consistency and provides a surface modification suitable for a range of biosensing or electrochemical applications. For example, the IrOx layer facilitates pH sensing. Also, the chemical properties of iridium oxide provide increased charge storage capacity which enables current injection for stimulation of the target site (optic disc) in the eye.

For glass ensheathed ultramicroelectrodes (UMEs) to be used in any electrophysiological application which involves reception or transmission of electrical signal through any length, the following characteristics are advantageous:
- a controllable frequency response input representing one side usually the one in contact with the biological/and or liquid sample,
- a well-insulated and electrical conductive length/body and a low-ohmic connection on the other side, usually the connection side or back-end.
- UME connection to any microscopic and/or macroscopic conductor by mechanical means either reversibly or non-reversibly preferably features a repeatedly deformable positively protruding mass from surface.

Glass ensheathed UMEs represent an ideal platform for optic disc stimulation because of their small size, massive scalability and ability to be interfaced with emerging high-channel count pixel drive/read-out technologies. UMEs feature small stray capacitances (e.g. less than 0.5 pFcm$^{-2}$) given the high insulator-conductor ratio, mechanical workability, broad material choice and commercial availability. UMEs usually have one dimension in the micrometre or nanometre domain and at least one in the millimetre or centimetre region, thus the properties of the electrified interfaces are to be carefully considered when high frequency electrical signal need to be passed by micron-sized or nano-sized interfaces.

Current challenges in optical stimulation and sensing miniaturisation are signal coupling and transport. The smaller the sensors are, the higher impedances (Z) become, resulting in significantly weakened signals and high noise levels. The interface's electrical coupling properties consequently bring limitations in the design of the drive/read-out electronics. Firstly, more amplifier stages and higher amplifier gains are required to condition the stimulus signals or recorded signals. Secondly, pre-filter and impedance matching circuitry are included to reduce ambient noise and pick up small-signals. Thirdly, power consumption of these additional amplifier stages could easily be a critical issue when limited power sources are available i.e. for battery powered implants~thus improving signal strength while keeping electrode dimensions in the micron and sub-micron domain is of paramount importance.

These issues can be addressed using a visual implant with micro-electrodes as discussed above. By performing a two-step surface modification of the tips of the UMEs at the front end, to include both a highly fractalized flake-like gold nano-structure layer and a second layer of highly porous metal oxide (e.g. iridium oxide), the impedance at the front end of the electrodes can be greatly reduced. This is shown in the graph of FIG. 4 which compares the impedance across different frequencies for three probes:

"polished Au"—a probe made of bare gold metal wires without surface modification of the tips at the front end "IrOx modified"—a probe where the tips of the wires at the front end have the IrOx layer but not the intervening gold nano-structure layer "JULIE"—a probe with electrodes as in the example of FIG. 10 with both the gold nano-structure layer and the IrOx layer at the front end tips of the wires.

As shown in FIG. 13, the impedance at the front end of the jULIE wires is an order of magnitude lower than the other types of wires. To test jULIEs we performed recordings in the olfactory bulb (OB) of anaesthetized mice (4-6 weeks old, Ketamine/Xylazine anaesthesia) using a Tucker Davis RZ2 amplifier with a PZ2 pre-amplifier and RA16AC-Z headstage. Extracellular spikes were reliably recorded with amplitudes of up to 1.6 mV. Consistent with this, when jULIEs were lowered several mm into the brain and returned to a superficial recording position, extracellular units were reliably recorded throughout the olfactory bulb. Due to the small size of the recording site and minimal damage to the tissue, jULIEs were found to be exceptionally suited for recording large amplitude (500-1500 µV), well isolated signals from the close vicinity of neurons (20-30 µm). FIGS. 14 and 15 show amplitudes of neuronal recordings made in a mouse brain using a typical commercially available probe and the JULIE probe respectively. As is clear from FIG. 15, the amplitudes recorded using the jULIE probe are much larger than the amplitudes shown in FIG. 14 for the commercial probe. Hence, signal to noise ratio can be improved and there is less need for additional amplification, helping to reduce power in battery-powered implants for example.

FIGS. 13-15 show results of using the electrodes for neuronal recording in the olfactory bulb. With neural sensing in the brain, the anatomical structure of the neuron cells does not match closely to the parallel arrangement of the wires in the bundle. In contrast, with stimulus of ganglion nerve axons in the optic disc or optic nerve, the axons also have a similar parallel side-by-side arrangement to the arrangement of the electrodes, so it is expected that it would be more straightforward to provide a low impedance interface between the electrodes of the implant and the axons when the implant is implanted into the eye. Hence, these electrodes 4 can also be used for a visual implant designed for optic disc stimulation. By enabling a reduced impedance connection to the target site in the eye, this reduces the need for as much amplification circuitry, hence saving power consumption and prolonging battery life.

Other advantages of the UME array 4 include:

(i) the dimensions of the penetrating wires are 2× to 5× times smaller and recording sites can be up to 50 times smaller (e.g. 1 µm) than in conventional probes. Also, the use of the Taylor-Ulitovsky method as discussed below results in wires with smoother sides than in conventional probes. This results in reduced tissue displacement and damage as well as in highly localized stimulation/recordings with better unit separation.

(ii) the nanostructured interface represents an excellent platform for further improved electrical coupling characteristics with the extracellular media, for example the nano-sized gold/IrOx interface allows for substantially higher signal-to-noise with amplitudes of up to 1.5 mV compared to typically 200-500 µV with conventional electrodes.

(iii) the material choice enables semi-automatic preparation for stimulus sites pre-arrangement to fit anatomical structures; and needle-like sharpening for seamless penetration of tissue.

(iv) there are also substantially improved charge transfer capabilities i.e. enabling current injection for stimulation purposes, in a highly localized manner.

FIG. 16 is a flow diagram illustrating a method of manufacturing the array of micro-electrodes 4 for the implant. At step 120 wire electrodes are formed using the Taylor-Ulitovsky method. The Taylor-Ulitovsky method is a technique for forming glass-sheathed wire electrodes with a very fine diameter, e.g. as small as a few microns. In the process, the metal or alloy conducting material is placed inside a glass tube which is closed at one end and the other end of the tube is heated to soften the glass to a temperature at which the conductor melts. The glass can then be drawn down to produce a fine glass capillary with the metal core inside the glass. Hence, metal cores of diameters in the range 1 to 120 microns can be coated with a glass sheath a few microns thick with this method. In particular, wires with a core in the range 1-10 µm surrounded in 10-40 µm of glass can be useful for electrical and electrochemical sensing. The metal used can include copper, silver, gold, iron, platinum, lead or other metals as well as crystalline or amorphous alloy compositions such as brass, bronze, platinum-iridium, or magnetic alloys.

At step 122, the electrodes are formed into a bundle or stack with the wires running parallel to each other. For example, the microwires can be machine wrapped into bundles of 10 s, 100 s, 1000 s, 10000 s or 100000 s of wire electrodes, to provide multiple channels for recording or cover the available contact portions on an integrated circuit.

At step 124, the relative positioning of the wire electrodes in the bundle may be adjusted using a magnetic field, as shown schematically in FIG. 17. As shown in the top part of FIG. 17, when the wire electrodes 104 with a substantially round cross-section are bundled together they will tend to pack together in a hexagonal packed arrangement, in which the electrodes in one row are offset relative to the electrodes in another row. However, for driving stimulus currents through the electrodes and/or reading out the signals measured using the electrodes, it can be useful to interface the wire electrodes with respective contact portions of an integrated circuit (IC), such as those used in multi-electrode arrays (MEA) and other pixelated integrated circuits. Most commercially available ICs have the pixelated contact portions of the readout circuits arranged in a two-dimensional square or rectangular grid pattern. Therefore, to match the industry standard rectangular contact point arrangement of an integrated circuit, it can be useful to reposition the wires in the bundle to form a square or rectangular grid pattern, in which the electrodes form rows and columns as shown in the right hand diagram at the top of FIG. 17. The lower part of FIG. 17 shows one technique by which this can be done. The wire electrodes 104 are wound through a passageway 130 having a square or rectangular cross section. For example, the passageway 130 may be a tube which could be enclosed on all four sides of the bundle, or could be missing one of the sides (e.g. winding the wires through the inside of a U-shaped bar can be enough). By applying a strong magnetic field (stronger than the electrostatics acting on the wires) to the wires as they pass through the gap, the relative positioning of the wire electrodes can be adjusted to form a square or rectangular grid array. For example, if the wires have gold cores, gold is a diamagnetic material and so a strong enough magnetic field can slightly repel the gold wires, and by pushing them up against the inside of a square or rectangular tube, this forces the wires into the desired square or rectangular grid arrangement.

Alternatively, step 124 can be omitted if the pitch of the wires within the bundle or the size of the gold contacts bumps at the back end of the wires will be sufficient that they can interface with a readout circuit regardless of the hexagonal packed arrangement.

At step 126 of FIG. 16, the bundle of wire electrodes is bonded together. This can be done in various ways. In one example, a filler material or adhesive may be introduced between the respective insulating sheets of the wire electrodes 104 to bond the electrodes together in the bundle. Alternatively, as shown in the example of FIG. 18, the wire electrodes can be bonded together by melting the insulating sheath of respective wires together so as to coalesce the insulator into a common matrix of insulating material surrounding the conducting wire electrodes. For example, this approach can be particularly useful when the insulating material is glass. Hence, as shown in the example of FIG. 18, the individual sheaths of the different wires are no longer visible and instead the wire electrodes are surrounded by a common insulating matrix of glass. This approach can be particularly useful for increasing channel density, because by avoiding the need to include a filler or adhesive between the respective wires, a greater number of electrodes per unit area can be included in the bundle.

Note that the wire electrodes do not need to be bonded along their full length. For example, it can be useful to leave a portion of the wire electrodes nearest the front end unbonded so that the free ends of the wire electrodes can spread out when inserted into a target sample, to increase the area over which recordings or current injection can be performed.

At step 128, a connection layer comprising metal nano-structures is deposited on the tips of the wire electrodes at the back end of the wires. The connection layer can be deposited by electrodeposition, in which the bundle of electrodes is held in a bath of electrolyte and a voltage difference is applied between the wire bundle and another electrode to cause ions in the electrolyte to be attracted to the wire electrode bundle, depositing a coating of metal nano-structures on the tip of each wire.

In one particular example, gold micro-hemispheres were deposited from a two-part aqueous cyanide bath containing 50 gL$^{-1}$ potassium dicyanoaureate(I) (K$_2$[Au(CN)$_2$]) and 500 gL$^{-1}$ KH$_2$PO$_4$ dissolved sequentially in deionized water (18 MOhm) (Tech, UK) at 60° C. All reagents were supplied by Sigma-Aldrich, UK, and were used without further purification. Prior to electrodeposition the polished substrate was washed with ethanol (90%), rinsed with deionized water, wiped with a lint-free cloth (Kimwipes, Kimtech, UK) and dried at 50° C. for 1 hour in an autoclave. The electrodeposition protocol was carried out with a VSP 300 potentiostat-galvanostat (Bio-Logic, France) controlled with EC-Lab (Bio-Logic, France) in a three-electrode cell setup composed of a gold UME bundle as working electrode (W$_E$), a coiled platinum wire (99.99%, GoodFellow, US) as counter electrode (C$_E$) and a Ag/AgCl|KCl$_{3.5M}$ reference electrode (REF) supplied by BASi, USA (E vs. NHE=0.205V). The REF was kept separated from the bath by a glass tube containing the support electrolyte and a porous Vycor glass separator. During gold deposition the W$_E$ potential was kept at E$_{red}$=−1.1V vs. REF for a time determined according to the desired size of the gold hemisphere to be formed. During electrodeposition the bath was thermostated at 60° C. under vigorous (500 rpm) stirring. This technique has been successful for many different types of metal conductor material, including gold, platinum, tin, copper, brass, bronze, silver and lead.

FIG. 19 is a graph showing how varying the time for which the electrodeposition is performed affects the size of the gold nano-structure bumps formed on the end of the wires. The upper line in FIG. 19 shows variation of the width of the gold bumps with electrodeposition time, and the lower line shows variation of the height of the bumps with electrodeposition time. Hence, the size of the gold bumps can be carefully controlled by varying the electro-deposition time.

Gold can be a particularly useful material for the back end connection layer. In contrast with their applications for the front end sensing, the connection of individual or high-count bundled UMEs to integrated circuitry is poorly examined and represents a significant drawback towards their usability in biomedical applications. In known interfacing methods for bonding individual or UMEs to macroscopic conductors or integrated circuitry, the main practices are based on soldering, conductive silver-epoxy bonding or mercury-dip. Although applied, these methods can easily increase the RC cell time constant at high frequencies given the stray capacitance at the glass-mercury/conductive epoxy junctions and are not relevant for reversible contacting individual or bundled UME assemblies; scaling such practices to high-count UME bundles (up to 1 million, for example) are a considerable engineering challenge. The state-of-the-art indium bump bonding developed for pixelated sensor and read-out chip interconnection employing photolithography, sputtering and evaporation or later electrodeposition could be a suitable processing practice, however due to indium's tensile and ductile properties, mechanical properties and overall tribological behaviour it cannot be applied as a reversible interconnection material in UME interfacing. Copper bumps as interconnects could be considered from a mechanical point of view, however given their possible diffusion into SiO in the presence of an electric field, breaking down transistor reliability, and affinity towards oxidation, make Cu a less attractive candidate as an interconnect material in physiological environments.

In contrast, gold is a promising contact material in medium wear conditions which can seamlessly enable reversible, scalable, low-cost, ultra-fine pitch and high yield bumping for interconnection purposes.

At step 132 of FIG. 16, an impedance reducing layer of metal or metal oxide nano-structures is deposited on the tips of the wire electrodes at the front end. This can be done by the same electrodeposition protocol as described above for step 128 for the back end. The material used for the nano-structures at the front end can be the same or different to the material used for the nano-structures at the back end, but in one example both use gold nano-structures.

At step 134 a functionalization layer is deposited on the impedance reducing layer at the front end. Again, this can be deposited by electrodeposition (although other techniques such as spraying could also be used). For example, a layer of metal oxide (e.g. iridium oxide) can be deposited on top of the gold nano-structures at the front end.

In one particular example, the electrodeposition protocol was carried out from a modified electrolyte solution based on a formulation reported by Meyer et al. (2001, "Electrodeposited iridium oxide for neural stimulation and recording electrodes", Neural Systems and Rehabilitation Engineering, IEEE Transactions on, 9(1), pp. 2-11), containing 10 $gL^{-1}$ iridium (IV) chloride hydrate (99.9%, trace metal basis, Sigma-Aldrich, Germany), 25.3 $gL^{-1}$ oxalic acid dihydrate (reagent grade, Sigma-Aldrich, Germany), and 13.32 $gL^{-1}$ potassium carbonate (99.0%, BioXtra, Sigma-Aldrich, Germany). Reagents were added sequentially to 50% of the solvent's volume first by dissolving IrCl in the presence of oxalic acid followed by the addition of $K_2CO_3$ over a 16 hour period until a pH=12 was reached. The electrolyte was aged for approximately 20 days at room temperature in normal light conditions until the solution reached a dark blue colour. IrOx was electrodeposited using a multichannel VSP 300 (Bio-Logic, France) potentiostat-galvanostat in 3 electrode cell setup comprising a glass-ensheathed Au wire bundle as working electrode (WE), a platinum rod (0.5 mm diameter, 99.95%, Goodfellow, US) as counter electrode, and Ag|AgCl|KCl/$_{3.5M}$ (Bioanalytical Systems, US) as a reference electrode (REF). The electrochemical protocol was composed of three consecutive stages combining galvanostatic polarisation (GP), cyclic voltammetry (CV) and pulsed potentiostatic protocols (PP). Between protocols open circuit voltage (OCV) of the WE was monitored for 180 second and represents the steady-state period. During galvanostatic deposition the WE potential was set to 0.8V vs. REF for 500 seconds. During CV deposition the WE potential was swept from −0.5V to 0.60 V vs. REF at 100 mVs in both anodic and cathodic direction. During the pulsed potentiostatic deposition the WE potential was stepped from 0V to 0.60V vs. REF with 1 seconds steps for 500 seconds.

As shown in FIG. 20, the tips of the wire electrodes at the front end can be polished/sharpened to provide a tapered surface that is angled to a point, to facilitate insertion into the target site within the eye.

The method of FIG. 16 may include an additional recess forming step 136 between steps 120 and 122. In step 136, part of the tips of the electrode is dissolved using a solvent to form a recess 140 in the end surface of the electrode 104 as shown in part a) of FIG. 21. For example, the recess can be formed by an electrochemical leaching step (e.g. by dissolving into an electrolyte in the presence of electrical current). The parts of the electrode 104 which are not to be dissolved may be masked by covering them with a mask material, so that only the portion at the end of the tip is dissolved. The subsequent steps of FIG. 16 are then performed on the wire electrodes having the recess in their tips. Therefore, as shown in part b) of FIG. 21, when the impedance reducing layer is subsequently deposited at step 128 of FIG. 16, the nano-structures 142 are deposited on the inside of the recess 140. The nano-structures 142 may also extend onto the surface of the electrode tip outside the recess. When the functionalization layer (e.g. IrOx) is then deposited on top of the impedance reducing layer at step 134, the functionalization layer 144 is deposited inside the recess. The functionalization material may also protrude out of the recess beyond the end of the electrode tip as shown in part c) of FIG. 21.

The approach shown in FIG. 21 provides several advantages. Firstly, providing a recess means that a greater volume of iridium oxide or other functionalization material can be deposited at the end of the electrode, which can improve the electrochemical properties of the electrodes. For example, given the available space, the charge capacity of the iridium oxide layer can be improved up to a 1000 times. Also, this approach provides robustness against mechanical deterioration of the electrode tips. During their working life, the electrodes may repeatedly be inserted into a sample and removed, and so the tips of the electrodes may gradually be worn away by contact against the sample, which can cause deterioration of the signals measured by the electrodes. By including the recess and depositing the surface layers inside the recess, then even if the end of the electrodes is worn down (e.g. so that the surface now is at the position indicated by the line 146 in FIG. 21), then there will still be a layer of the impedance reducing nano-structures and a layer of the functionalization material at the end of the electrodes, so that the electrode can still perform its function. Therefore, the recessed design helps to increase the electrodes' lifetime.

A similar recess may be formed at the back end of the electrodes, with the connection layer of metal nanostructures formed at least partly inside the recess. Again, this helps provide robustness against mechanical deterioration, which could otherwise wear away the connection layer if the connection layer is repeatedly pressed against the contact bumps of pixel readout circuits as discussed below.

The integrated circuit 150 used to drive stimulation currents and/or read out and amplify signals measured using the UME array 4 can be implemented in different ways. For stimulation purposes, the IC may be a pixelated display driver, such as the CMOS based circuits for driving LED or OLED displays. For readout of measured signals, the IC 50 may be a multi electrode array (MEA), a CMOS based potentiostat or a pixelated photodetector. All these are already available commercially and therefore it is not necessary to design a bespoke circuit for this purpose, which reduces the cost of implementing an apparatus for electrochemical measurements. If both stimulation and readout is required, then a subset of pixels of the IC corresponding to the stimulation electrodes may be implemented similar to a pixel of a display driver, while another subset of pixels of the IC corresponding to readout electrodes may be implemented similar to an element of a multi-electrode array, CMOS based potentiostat or pixelated photodetector. FIG. 22 shows how the micro-electrode array 4 may be interfaced with the integrated circuit 150. As shown in FIG. 22, the gold contact bumps 158 at the back ends of the respective wire electrodes 104 can simply be pressed directly against the contact bumps 154 of the respective pixel driving/readout circuits 155 of the IC 50 to provide the electrical connection between the wires and corresponding pixels (without any interposing connector unit between the wire bundle and the IC 150). Hence, the integrated circuit provides a multi-channel amplification and readout system for reading the electrode signals from the respective wires. It is not essential that every pixel driving/readout circuit of the IC 150 interfaces with a corresponding wire electrode. Depending on the arrangement of the wires within the bundle, it is possible that some pixel readout circuits may not contact a corresponding wire.

An alternative is that the wires can also be embedded in a second cladding holding wires together and have the bumps for connection.

For wire bundles with relatively low channel count (e.g. less than 1000 wires in the bundle), it may also be possible to individually bond each wire to connectors in the integrated circuit. However, when the channel count is higher (e.g. greater than 1000 wires), then it becomes increasingly impractical to individually bond each wire, and in this case the approach shown in FIG. 22 may be more useful, whereby the bumps on the end of each wires are simply pressed against the contact portions of a pixelated integrated circuit.

In the above examples, the functionalization layer is made of iridium oxide. However, this is just one example and other types of functionalization layer could also be used. The functionalization layer may be selected according to the intended purpose of the respective electrodes. Different electrodes of the array could have different types of functionalization layer deposited on top of the impedance-reducing gold nano-structure layer at the front end of the electrodes. For example, the same array could include a mixture of electrodes designed for visual stimulation (e.g. with IrOx functionalisation layer) and electrodes designed for sensing target substances or conditions. One advantage of using gold as the nano-structure impedance reducing layer is that gold nano-structures provide a good platform for a range of different functionalization layers for different biosensing or electrophysiological purposes. For example, the functionalization layer may include other metal oxides, such as copper oxide (useful for sensing glucose) titanium dioxide or manganese oxides, or could include other substances such as carbon nanotubes, graphene, ATP, DNA or other nucleic acids, proteins etc.

Another example of a functionalization layer may comprise self-assembled monolayers. Self-assembly describes the spontaneous formation of discrete nanometric structures from simpler subunits. During the process of self-assembly, atoms, molecules or biological structures form a more complex secondary layer with fewer degrees of freedom due to packing and stacking. The simplest self-assembled systems are self-assembled monolayers (SAMs). SAMs are formed by the adsorption of molecules on solid surfaces and are governed by intermolecular forces. The most popular molecules forming SAMs are thiols and dithiols: in biology and medicine these molecules are used as building blocks for the design of biomolecule carriers, for bio-recognition assays, as coatings for implants, and as surface agents for changing cell and bacterial adhesion to surfaces. Hence, by covering the layer of metal or metal oxide nanostructures (e.g. the nano-rough gold deposits) on the tip of the microwires with SAMs, we can functionalise the tip and build up a highly specific bio-sensitive layer. This can enable the identification of DNA fragments, biomolecules or analytes present in tissue, bodily fluids, or nerves.

Hence, by providing different functionalization layers, the implant may function as a wide variety of electroceutical devices (devices which employ electrical stimulation to affect or modify functions of the body) or instruments for recording data about electrical or electrochemical properties of the sample in which the electrodes are inserted. In some examples, the visual implant may have a dual function, acting as both an electroceutical device and a recording instrument. Alternatively, other embodiments could solely act as a visual implant with no recording functionality.

Where different types of micro-electrodes are bundled together (e.g. some stimulation electrodes and other electrochemical sensing electrodes), different approaches may be used to assemble the different types of electrodes in the implant. In one example, the array 4 may be formed from a number of different subsets of electrodes, each subset having different types of functionalization layer deposited on the top of the gold nano-structure impedance reducing layer at the front end of the wires. For example, a number of bundles may be manufactured separately using the process described above, each having a different type of functionalization layer, and then the respective bundles can be assembled into a probe, to allow a single probe to make two or more different types of electrochemical measurements. For example, a bundle may be provided with iridium oxide functionalization layer may provide stimulating currents for visual stimulation or may sense pH or electrical currents, while another bundle may have copper oxide or graphene functionalised wires for glucose sensing, etc. The bonding of the different subsets of wire electrodes could be done through an adhesive or a filler layer, or by melting the glass insulating sheaths of the wires together.

In another alternative, instead of forming the respective bundles 82 separately and then assembling them together, a single wire bundle could be made with different functionalization layers on respective wires of the bundle, for example by masking some wires during the step of depositing the functionalization layer or by ensuring that the electrodeposition current is only applied to some of the wires, with multiple functionalization deposition steps for the different types of functionalization layer.

As shown in FIG. 23, in addition to the wire electrodes 104 having a conducting core 106 surrounded by an insulating sheath 108, the micro-electrode array 4 may also include hollow-core channels 170 which comprise a hollow core (made of air) surrounded by a sheath of the same insulating material 108 as used for the wire electrodes 104. The hollow-core channels 170 are arranged parallel to the wire electrodes 104. For example, the hollow-core channels 170 can be formed by providing some wires in the bundle with a solid core of soluble material clad in an insulating sheath, and bundling these together with the conducting-core electrodes 104 in a desired pattern, and then dissolving the core of the hollow-core channels 170 to leave an empty void at the centre of these channels. The hollow-core fibres 170 can be useful for both delivery and extraction of liquid or almost liquid phase substances from the surface or interior of virtually any biological media. For example, they could be used as micro-fluidic channels for local delivery of pharmaceuticals, molecules, cells, genes, tissue. For example, the implant 2 could include a reservoir from which the substance to be supplied into the tissue is drawn by the hollow-core channels 170 of the array 4. The substance to be delivered can be injected into the reservoir by a needle when the implant is in position.

FIG. 24 shows an example in which the wire electrodes 104 (including both their core 106 and the insulating sheathes 108) are partially embedded in a block of cladding material 250 along part of their length, with gaps 252 between the respective wire electrodes along a remaining part of their length. The layer of nanostructures or other modifications at the tips of the electrodes are not shown in FIG. 24 for conciseness, but it will be appreciated that the tips of the electrodes can be modified in the same way as in any of the examples described above. The cladding material 250 provides a rigid support for the electrodes to prevent separation of the bundle of wire electrodes 104, while providing gaps between the free ends of the electrodes 104 can be useful for allowing some separation of the wire electrodes when inserted into a sample (e.g. the insulating material may be a flexible material), increasing the area over which the wire electrodes can gather measurements or provide stimulation. Although FIG. 24 shows an example where the cladding material 250 is formed at the back end of the probe, in other examples the cladding material 250 could be at a mid-point of the electrodes so that both ends of the wire electrodes may be free to move as there are gaps between the insulating sheaths of the wires.

FIG. 24 shows an example process for manufacturing the probe with flexible wire electrodes 104 held together by a block of rigid cladding material 250. As shown in the left hand part of FIG. 24, initially the wire electrodes may be formed individually with the core 106 surrounded by a first sheath 108 of insulating material and a concentric second sheath 256 of cladding material outside the first sheath 108. The cladding material may be more soluble to a given solvent than the insulating material used for the first sheath 108. Other than the solubility, it is preferable if the cladding material is similar in physical properties to the insulating material, e.g. similar in thermal expansion and composition. The wires 104 are bundled together parallel to each other, and heat is applied to melt the second cladding layer 256 together to form a block of melted-together cladding 250 with the wires 104 of core material 106 and insulating material 108 embedded inside the cladding block. A solvent which can dissolve the cladding but not the insulation is then applied to dissolve part of the cladding block 250 down to a given level, preserving the initial ordering and parallel stacking of the wires and leaving the free end of the wires with gaps 252 in between while a bound section of wires is surrounded by the cladding block 250. These steps are valid in a range of possible geometries, e.g. hemispherical, saw-like, planar, random or combined.

In summary, by providing a visual implant comprising a number of micro-electrodes made of conducting material and insulating material surrounding the conducting core, with a layer of metal or metal oxide nano-structures deposited on the tips of the wire electrodes at the front end of the wire bundle, this can provide much lower impedance, increasing the signal/noise ratio of currents transmitted for stimulation purposes. The core material may be one of gold, platinum, copper, brass, nickel, tin, silver, iron, lead, brass, bronze, platinum-iridium, silver-lead for example. The insulating material may be glass or plastic, for example.

In some examples the wire electrodes may have separate insulating sheaths of the insulating material. Alternatively, the wire electrodes may be disposed in a common insulating matrix of insulating material, which can be formed for example by melting the glass sheaths of the individual wire electrodes together as discussed above.

The metal or metal oxide used for the nano-structures in the impedance reducing layer could be any of the following: gold, platinum, ruthenium, titanium, iridium, indium, manganese, or oxides of such materials such as manganese oxide or ruthenium oxide. In particular, using nano-structures made of a noble metal, such as gold or platinum, can be particularly useful for reducing the impedance. In particular, gold nano-structures have been found to be particularly effective as shown in the graph of FIG. 13.

The layer of metal or metal-oxide nano-structures formed at a front end of the wire bundle may act as an impedance reducing layer for reducing impedance at the interface with the sample being measured, and also can act as a surface for functional modifications.

Also, at the back end of the micro-electrodes there may be a connection layer of metal nano-structures on tips of the wire electrodes. This end is used as the back end of the probe for outputting signals to readout electronics. The nanostructures in the connection layer at the back end of the wire bundle may be made of the same material as the nanostructures in the impedance reducing layer at the front end, or alternatively the respective ends of the wire bundles may be provided with nanostructures of different materials (e.g. gold at the front end of the probe and platinum at the back end). Metal oxides may be less preferred for the back end as they may increase the resistance of the electrical connection, whereas for the front end they may be useful for bring down impedance because of the increase in the specific surface given their porous structure. For the back end, a nanostructured surface can be advantageous because on compression it compacts instead of cracking.

In some examples, a layer of the metal or metal oxide nano-structures may be formed at the front end of the wire bundle, and a layer of metal nano-structures may be formed at the back end of the wire bundle.

One or both of the layers of nano-structures formed at the front and back ends of the wires may be formed from separate bumps of nano-structures, with each bump formed on the tip of a respective wire electrode. The bumps may have a rounded or hemispherical profile.

A functionalization layer may be deposited on the layer of metal or metal oxide nano-structures at the front end of the wire bundle.

For at least one of the wire electrodes, the tip of the electrode at the front end may comprise a recess, the layer of nano-particles may be deposited on the inside of the recess. If provided, the functionalization layer may be formed on top of the layer of nano-particles inside the recess. The functionalization layer may protrude out of the recess.

The wire bundle may in some examples comprise a first subset of wire electrodes with a first type of functionalization layer deposited on the layer of nano-particles at said front end of the bundle, and a second subset of wire electrodes with a second type of functionalization layer deposited on the layer of nano-particles at said front end of the bundle. In some cases there may be three or more subsets of wire electrodes with different types of functionalization layer.

In one example, the wire electrodes may be ultramicroelectrodes (UMEs). The wire electrodes may have a diameter less than or equal to 30 µm. In other examples, the wire electrodes may be even narrower, for example with a diameter less than or equal to 25 µm, less than or equal to 20 µm, less than or equal to 15 µm, less than or equal to 10 µm or less than or equal to 5 µm. By providing an implant with smaller diameter wires than previous techniques, this enables a great increase in channel count in an implant of a given size, and also means less current needs to be transmitted through a given wire (the reduced impedance at the front end also helps reduce the current required), so that less tissue damage may be caused.

The nanostructures in the respective layers at each end of the probe may have a unit width less than or equal to 500 nm. More particularly, the unit width may be less than or equal to 400 nm, less than or equal to 300 nm, less than or equal to 200 nm, less than or equal to 100 nm or less than or equal to 50 nm. The term "unit width" refers to the width across the longest dimension of an individual nano-structure (e.g. an individual flake, grain or nanoparticle), not the width of the mass of nano-structures as a whole. In some cases the nano-structures at the front end may have a unit width which is less than or equal to 20% of the wire diameter of the electrodes, less than or equal to 15% percent of the wire diameter, less than or equal to 10% of the wire diameter, or less than or equal to 5% of the wire diameter. The nanostructures at the back end can also be less wide than the wire diameters of the electrodes, or alternatively can cover a greater area of the tips of the wire electrodes, and could cover the entire tip. Note that the different nano-structures within the layer will in practice have different unit widths to each other, but all the nano-structures may have a unit width defined within the thresholds described above. Similarly, the functionalization layer may also comprise a layer of nanostructures (e.g. of Iridium oxide, or another material), which may have unit widths as defined within the thresholds described above. The nano-structures in the functionalization layer may be of a different size to the nano-structures in the impedance reducing layer or connection layer.

The tips of the wires may be sharpened, or have a tapered end which meets at a point, to facilitate insertion into the target site within the eye.

Another aspect of the invention relates to an implant as described herein for performing a diagnostic or therapeutic operation on a subject. Another aspect of the invention relates to a method of using an implant as described herein for performing a diagnostic or therapeutic operation on a subject. Preferably, the subject is a human or animal subject, more preferably, a human. Preferably, for this embodiment, the method comprises introducing the implant into the subject, more preferably into an eye, more preferably with the electrodes inserted into the optic disk or optic nerve. More preferably, the method further comprises the steps of transmitting current into the subject using the implant and/or reading out current from the subject using the implant.

In one aspect of the invention, the electrochemical probe described herein is for, or for use in, various methods of treatment, including but not limited to, artificial visual implants or eye implants.

In another embodiment, the invention relates to a method of delivering a drug to a subject, said method comprising contacting the subject with an implant as described herein, wherein the drug is present in or on the implant. Preferably, the drug is released at a localised target site in the subject. By way of illustration, drug molecules can be delivered to a target site via hollow channels in parallel with the stimulation electrodes or readout electrodes. In one embodiment, the drugs are delivered in liquid form, e.g. by injection into a reservoir within the implant, and are released through the hollow channels into the target site. Alternatively, drug molecules can be attached to the surface of one or more micro-electrodes via a linker moiety or other substance which can be activated by supplying a current pulse to the probe to release the drug. Another aspect of the invention relates to an implant as described herein which is used in conjunction with one or more therapeutic agents. Thus, another embodiment relates to an implant as described herein for use in treating a proliferative disorder in a subject, wherein said implant delivers one or more therapeutic agents to the subject.

In another aspect of the invention, the implant described herein is for, or for use in, the detection of various substances in a sample, or in a subject, including but not limited to, protons (e.g. detecting pH), biological substances (e.g. proteins, glucose, neurotransmitters, hydrogen peroxide, tissue modulators, calcium, nitric oxide, DNA/RNA, immunological molecules) and/or toxins (e.g. heavy metals). Preferably, the detection takes place in vivo. Thus, in one embodiment, the invention relates to a method of detecting a substance as defined above in a subject, said method comprising contacting the implant with a tissue or organ of the subject. By way of illustration, in order to detect or sense a change in pH, the electrodes can be modified using iridium oxide, for example, by coating at least a portion of the electrodes with iridium oxide. For alcohol detection, the electrodes can be functionally modified with one or more alcohol oxidases, for example, by attaching an alcohol oxidase to the probe using a suitable linker moiety. Other substances/molecules (e.g. enzymes, proteins, RNA, DNA, oligonucleotides, graphene, copper oxide, etc.) can also be attached to the surface of the micro-electrode tips in a similar manner. The skilled person would understand that selected electrodes of the implant can be tailored to detect a particular substance or molecule and would be familiar with literature methods for functionally modifying the surface of the electrodes.

In another aspect, the invention relates to one or more diagnostic methods using the implant described herein. For example, in one embodiment, the implant can be used to detect changes in the subject, such as changes associated with diabetes, including by detecting changes in the level of one or more biomarkers (e.g. glucose), for example in the bloodstream of the subject.

FIGS. 25 to 29 illustrate results of an in-vivo experiment showing use of a micro-electrode array as discussed above for highly localised deep brain stimulation in the olfactory cortex of a Tbet-GCaMP transgenic mouse, which has been genetically modified so that its cell membranes include a protein (GCaMP) which is an indicator of neuron activity. This imaging technique is based on the principle that neural activity causes rapid changes in intracellular free calcium, so that calcium imaging experiments can track the activity of neuronal populations and probe excitation of small neurons. Genetically-encoded protein sensors can be targeted to specific cell types for non-invasive imaging of identified neurons and neuronal compartments over chronic timescales. Calcium indicator proteins include the single fluorophore sensor GCaMP and several families of Förster resonance energy transfer based sensors. Hence, in the Tbet-GCaMP transgenic mouse, stimulation of neurons produces changes in calcium levels causing fluorescence of GCaMP which is visible in the images shown in FIG. 25 captured using two-photon excitation microscopy.

The upper image in FIG. 25 shows the position of the probe (see the dotted lines at upper part of image and ellipse showing the position of the probe tip), as well as numbered labels of particular cell locations. The bottom left image shows the two-photon imaging field of view when no stimulation current is applied through the micro-electrode array. The bottom right image shows the corresponding two-photon imaging field of view when a stimulation current of several tens of microamps is applied. All three images have the same field of view. As shown from the comparison between the OFF and ON images, clearly definable neural activity is caused by the stimulation, especially for the cells labelled with white arrowheads, for which the intensity of fluorescence is brighter in the right hand image compared to the left hand image. As shown from the comparison with the top image, a response is visible even for cells which are some distance away from the location of the probe tip.

FIG. 26 is a set of graphs showing the response at a given region of interest (ROI 5) within the field of view of FIG. 25, when stimulation currents of different magnitudes from 20 µA to 50 µA are applied. The x-axis is time and the y-axis is dF/F, the change in fluorescent intensity (pixel brightness) expressed as a ratio relative to the average intensity when no stimulation is applied. FIGS. 27 and 28 show corresponding sets of graphs for two further regions of interest (ROI 6 and 10 respectively). FIGS. 26 to 28 show that neurons in the field of view responded to monopolar electrical stimulation using the micro-arrays discussed above. It has been found that some cells respond to very small currents, while other cells response at larger currents. FIG. 29 shows the response to different currents for the three regions of interest shown in FIGS. 26 to 28, as well as three further regions of interest. The y-axis in FIG. 29 is the integral of dF/F over time within the time period shown in the shaded region of the graphs in FIGS. 26 to 28 (and corresponding time periods for ROIs 15, 26, 33). FIG. 29 shows that neural activity can be elicited reliably between 20 µA to 50 µA, and that in particular neurons respond to a 50 µA square pulse irrespective of their volumetric arrangement with respect to the stimulation site. Hence, it is demonstrated that in-vivo stimulation of neurons is possible using an implant having the micro-electrode array as discussed above.

FIGS. 30 to 33 show a further experiment in which a spaced ~1000-channel micro-electrode array is acutely placed on the optical nerve head in a sheep's eye. FIG. 30 shows an optical microscopy image of an array of around 1000 micro-electrodes placed over the half of the optic-nerve head in an in-vitro preparation, ready for insertion into the nerve head (optic disk). Inset (B) of FIG. 30 shows the initial size and shape of the nerve head, showing that while a 1000-channel probe has been chosen here, there would be space for 2-3 times more channels if desired. FIG. 31 shows a micro-CT scan of the micro-electrodes when inserted into the optic nerve head. The images labelled XZ, XY, YZ show the side view of the micro-electrode array, and images of the front-end and back-end of the micro-electrodes respectively. The unlabelled figure represents the rendered 3D composition.

FIG. 32 shows further images of the experimental set up where a subset of nerve fibers are stimulated. The jULIEs stimulation probe comprises a 10-channel micro-electrode array of the type discussed above (with Taylor-Ulitovsky wires deposited with gold nano-structures on the tips of the wires), which is inserted into the nerve head in the sheep's eye. By stimulating the ganglion cell axons in the nerve head directly, there is no need to consider the response of the retinal cells when developing visual implants, as the retinal cells can be bypassed. This will make development of visual implants more straightforward than if the retinal response also had to be considered in the model for mapping desired image sensations to a pattern of stimulation current. In another example, using said wires, stimulation can also work in combination when a subset of the array channels stimulate the retina or fovea in combination with the optic disc stimulation.

For recording the effect of the stimulation applied by the stimulation probe, a recording probe ("jULIEs recording probe") is provided, which also comprises a micro-electrode array of the type discussed above, although in this case with 16 recording channels, rather than ~10 in the stimulation probe. The recording probe is inserted into the optic nerve around 2 cm away from the eyeball. The recording probe is used to measure the stimulation intensity when stimulation current is supplied by the stimulation probe.

The top image of FIG. 33 shows the recorded stimulation intensity when a series of 10×1 ms×40 µA square pulses were injected through the optic disk and recorded downstream at the far side of the optic nerve. The lower image of FIG. 33 shows the recorded stimulation intensity when the magnitude of the 10×1 ms pulses is increased to 165 µA. As shown in both images, the stimulation probe is clearly able to elicit a measurable response in the optical nerve. Hence, this demonstrates the principle that by inserting the micro-electrode array of the type discussed above with the wires parallel to the ganglion nerve axons in the optic disk, it is possible to transmit signals along the optic nerve which are sensed downstream in the optic nerve.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

The invention claimed is:

1. A visual implant comprising:
   an array of micro-electrodes including at least two stimulation micro-electrodes each comprising:
      a core of conducting material;
      insulating material surrounding the core; and
      a layer of metal or metal oxide nano-structures deposited on tips of the micro-electrodes at a front end for interfacing with a target site for visual stimulation; and
   an integrated circuit to control a pattern of stimulation current driven through the array of micro-electrodes.

2. The visual implant according to claim 1, in which the micro-electrodes have a diameter less than or equal to 30 µm.

3. The visual implant according to claim 1, in which the at least two stimulation micro-electrodes also comprise a connection layer of metal nano-structures deposited on tips of the micro-electrodes at a back end for interfacing with the integrated circuit.

4. The visual implant according to claim 1, in which the nano-structures at the front end comprise nano-structures made of a noble metal.

5. The visual implant according to claim 4, in which the noble metal comprises gold.

6. The visual implant according to claim 1, in which the at least two stimulation micro-electrodes also comprise a functionalisation layer deposited on the layer of metal or metal oxide nano-structures at the front end.

7. The visual implant according to claim 6, in which the functionalisation layer comprises iridium oxide.

8. The visual implant according to claim 1, in which the insulating material comprises glass.

9. The visual implant according to claim 1, in which the micro-electrodes are mechanically flexible.

10. The visual implant according to claim 1, in which the at least two stimulation micro-electrodes comprise Taylor-Ulitovsky wires.

11. The visual implant according to claim 1, in which tips of the micro-electrodes at the front end have a polished angled tip surface with a sharpened point, and for the at least two stimulation micro-electrodes the metal or metal oxide nano-structures are formed on the angled tip surface.

12. The visual implant according to claim 1, in which the integrated circuit comprises a pixel display driver comprising a plurality of pixel units for driving respective pixels of a display.

13. The visual implant according to claim 1, in which the integrated circuit is configured to perform simultaneous driving of current through stimulation micro-electrodes arranged in a two-dimensional pattern.

14. The visual implant according to claim 1, in which the integrated circuit is configured to receive image information indicative of a captured image, and to control the pattern of stimulation current based on the received image information.

15. The visual implant according to claim 14, comprising a wireless communication unit to receive the image information from an external image capture device.

16. The visual implant according to claim 14, comprising an image capture unit to capture the captured image and processing circuitry to process the captured image to generate the image information based on the captured image.

17. The visual implant according to claim 14, comprising processing circuitry to detect features in the captured image indicated by the image information and to determine a pattern of stimulation current to be applied to the at least two stimulation micro-electrodes based on the detected features.

18. The visual implant according to claim 17, in which the features comprise edges, gradients, shades or colours.

19. The visual implant according to claim 17, in which the processing circuitry is configured to modulate at least one of a spatial position, frequency, and intensity of the stimulation current applied to the at least two stimulation micro-electrodes based on the detected features.

20. The visual implant according to claim 1, in which the array also comprises at least one sensing micro-electrode, and the integrated circuit is configured to control supply of current to, or readout of voltage or current from, the at least one sensing micro-electrode for sensing a predetermined substance or condition.

\* \* \* \* \*